(12) United States Patent
Discenzo

(10) Patent No.: US 6,980,298 B2
(45) Date of Patent: *Dec. 27, 2005

(54) SYSTEM FOR MONITORING SEALING WEAR

(75) Inventor: Frederick M. Discenzo, Brecksville, OH (US)

(73) Assignee: Reliance Electric Technologies, LLC, Mayfield Heights, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/430,722

(22) Filed: May 6, 2003

(65) Prior Publication Data

US 2003/0202188 A1  Oct. 30, 2003

Related U.S. Application Data

(60) Division of application No. 09/624,654, filed on Jul. 25, 2000, now Pat. No. 6,580,511, which is a continuation-in-part of application No. 09/504,440, filed on Feb. 16, 2000, now Pat. No. 6,359,690, which is a continuation of application No. 09/253,785, filed on Feb. 22, 1999, now Pat. No. 6,067,159, which is a continuation of application No. 08/959,610, filed on Oct. 28, 1997, now Pat. No. 6,111,643.

(51) Int. Cl.[7] ............................................. G01B 9/02
(52) U.S. Cl. ................................................... 356/477
(58) Field of Search ............................... 356/35.5, 477, 356/496; 250/227.14, 227.11, 227.16, 227.19; 73/52

(56) References Cited

U.S. PATENT DOCUMENTS

| 3,679,277 | A | * | 7/1972 | Dohmen ..................... 384/480 |
| 4,414,012 | A | * | 11/1983 | Suto et al. ..................... 65/414 |
| 4,433,198 | A | * | 2/1984 | Berner et al. ............... 136/230 |
| 4,460,893 | A | * | 7/1984 | Thomas et al. ............. 340/682 |
| 4,657,091 | A | * | 4/1987 | Higdon ....................... 175/229 |
| 4,884,434 | A | * | 12/1989 | Satake et al. ..................... 73/7 |
| 5,361,130 | A | * | 11/1994 | Kersey et al. .............. 356/478 |
| 5,438,860 | A | * | 8/1995 | Kawai et al. ..................... 73/7 |
| 5,473,428 | A | * | 12/1995 | Lee et al. .................... 356/480 |
| 5,818,585 | A | * | 10/1998 | Davis et al. ................ 356/477 |
| 5,844,667 | A | * | 12/1998 | Maron ....................... 356/35.5 |
| 6,080,982 | A | * | 6/2000 | Cohen .................... 250/227.11 |
| 6,580,511 | B1 | * | 6/2003 | Discenzo .................... 356/477 |
| 6,615,639 | B1 | * | 9/2003 | Heinzen .......................... 73/7 |

* cited by examiner

*Primary Examiner*—Andrew H. Lee
(74) *Attorney, Agent, or Firm*—Amin & Turocy LLP; Alexander M. Gerasimow

(57) ABSTRACT

A system for determining at least one condition of a seal including an optical fiber for transmitting light from a light source. The optical fiber is embedded in the seal and operatively coupled to an interferometric system. The interferometric system is operatively coupled to a processor. The interferometric system provides the processor with information relating to wear of the optical fiber, and the processor determines wear of the seal, rate of wear and remaining useful life of the seal based on the information relating to wear of the optical fiber.

28 Claims, 24 Drawing Sheets

| | VIBRATION | BRUSH PRESSURE (LIGHT) | UNBALANCED SHUNT FIELD | ARMATURE CONNECTION | LIGHT ELECTRICAL LOAD | ELECTRICAL OVERLOAD | ELECTRICAL ADJUSTMENT | CONTAMINATION | | BRUSH TYPE | |
|---|---|---|---|---|---|---|---|---|---|---|---|
| | | | | | | | | GAS | ABRASIVE DUST | ABRASIVE BRUSH | POROUS BRUSH |
| PITCH BAR-MARKING | ▨ | ▨ | ▨ | ▨ | | | | | | ▨ | |
| SLOT BAR-MARKING | | ▨ | | | | ▨ | ▨ | ▨ | | | |
| COPPER DRAG | ▨ | ▨ | | | | | | ▨ | | ▨ | |
| STREAKING | | ▨ | | | ▨ | | | ▨ | ▨ | | ▨ |
| THREADING | | | | | ▨ | | | ▨ | ▨ | | ▨ |
| GROOVING | | | | | | | | | | ▨ | |

Fig. 8

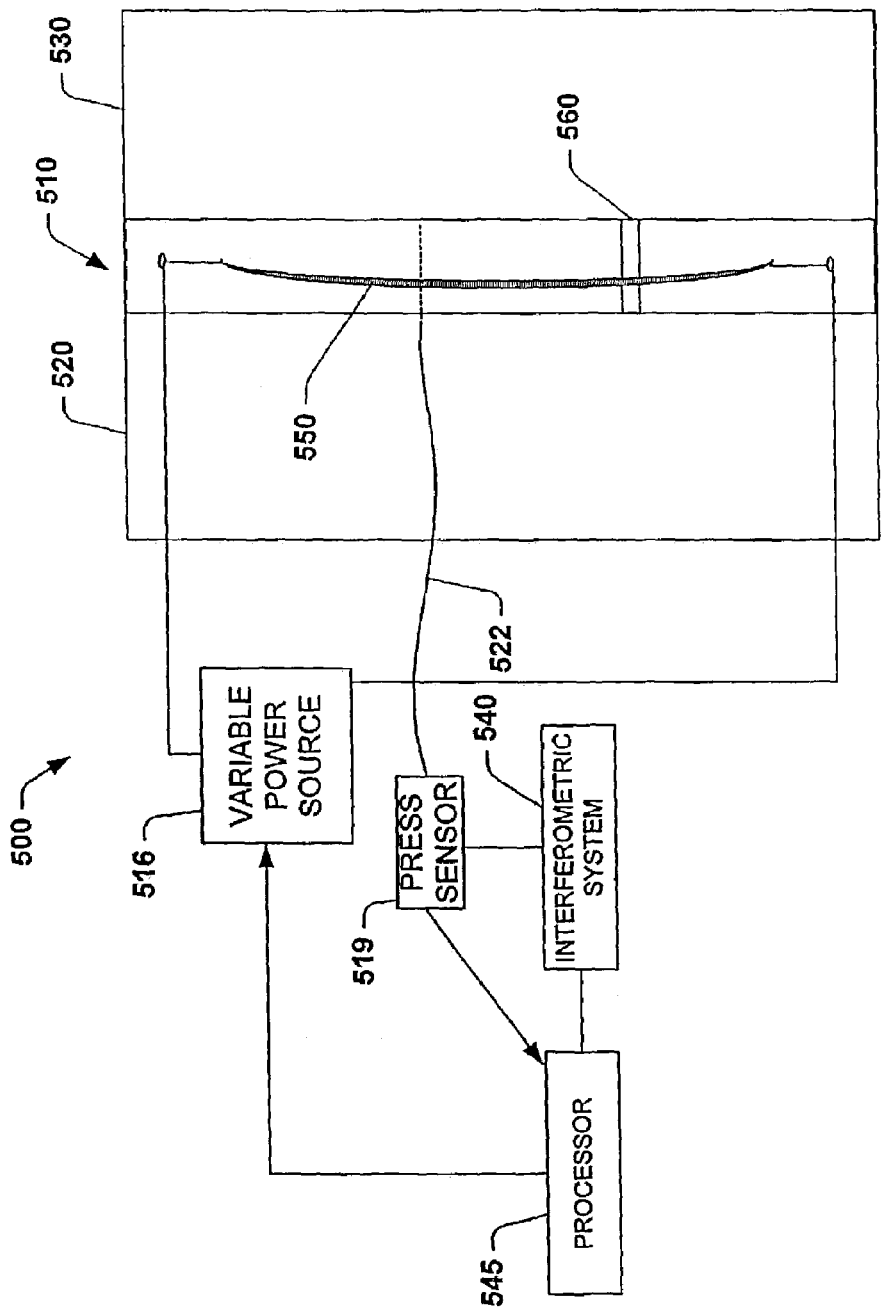

SYSTEM FOR MONITORING SEALING WEAR

CROSS REFERENCE TO RELATED APPLICATIONS

This application is a divisional application of U.S. patent application Ser. No. 09/624,654 filed Jul. 25, 2000, now U.S. Pat. No. 6,580,511, entitled SYSTEM FOR MONITORING SEALING WEAR., which is a continuation-in-part (CIP) of U.S. patent application Ser. No. 09/504,440 filed Feb. 16, 2000, now U.S. Pat. No. 6,359,690, entitled APPARATUS, SYSTEM AND METHOD FOR DETERMINING WEAR OF AN ARTICLE, which is a continuation of U.S. patent application Ser. No. 09/253,785 filed Feb. 22, 1999 entitled SYSTEM FOR DETERMINING WEAR OF AN ARTICLE (which issued as U.S. Pat. No. 6,067,159), which is a continuation of U.S. patent application Ser. No. 08/959,610 filed Oct. 28, 1997, now U.S. Pat. No. 6,111,643, entitled APPARATUS, SYSTEM AND METHOD FOR DETERMINING WEAR OF AN ARTICLE.

TECHNICAL FIELD

The present invention generally relates to an apparatus, system and method for determining wear and the rate of wear of an article such as for example a seal, a bearing, a carbon brush, a brake pad or tire.

BACKGROUND OF THE INVENTION

Dynamoelectric machines such as direct current (DC) motors use carbon brushes to provide a means for transferring current from an external source to a rotating armature of the motor. The brushes are typically made of a carbon particulate such as graphite and a binder material and may also include metallic particles.

These brushes are typically spring loaded to maintain good electrical contact with a commutator (i.e., slip ring) of the motor. A follower spring is employed to apply a biasing force against the rear end of the brush to cause the other end of the brush to be pushed into contact with the commutator. Since the commutator is in motion relative to the brushes in contact therewith, the brushes wear down over time. Consequently, these brushes must be replaced before they are completely worn in order to protect the commutator of the motor against damage. When worn excessively, continued operation will result in the metallic brush holder or follower spring assembly contacting the rotating commutator causing costly damage to the soft commutator bars, brush system or both. Alternating current (AC) machines and generators may similarly employ brushes and commutators for the transfer of electric power and have similar brush wear problems.

Because the operating life of carbon brushes depends, respectively, upon the type of operation and environmental conditions of the installed motor and the desire to utilize the brushes to the maximum possible extent without risk to the commutator, it is good practice to monitor the carbon brushes for a predetermined amount of wear.

Cut-off carbon brushes are occasionally employed which automatically switch off a motor when a predetermined amount of wear of the carbon brushes has been reached. However, in the absence of expensive and time-consuming intermediate inspections, it is unforeseeable when the motor will be switched off. As a result, a process incorporating such a device must take into account the risk of unexpected shutdown of the motor due to brush wear.

Carbon brushes with alarm devices which provide an early warning of the failure due to wear are available. These devices typically include an alarm contact provided by an insulated electrical conductor (e.g., a copper strand) inserted into the upper end of the carbon brush away from the commutator. When the brush wears by a predetermined amount, the electrical conductor contacts the commutator (or slip ring) which serves to complete an electric circuit or, as by wearing through a loop at the end of the conductor, break an existing circuit. A problem with such a device is that the electrical conductor may cause some damage to the commutator surface if exposed to it for an extended period of time as a result of metal to metal contact. Furthermore, such devices only alert a user that the brush has reached a particular level of wear—such alarm system does not provide a user with the rate of wear of the carbon brush or any type of intermediate evaluation.

Another type of article that is prone to frictional wear is a brake pad. Brake pads in automobiles, for example wear through usage and require periodic replacement. Inspection of brake pads requires the removal of the wheel from the vehicle so that a visual examination may be performed. Many individuals are unwilling and/or unable to perform the inspection or not skilled enough to know what to look for when the wheel is removed.

Many vehicle owners may rely on a dashboard trouble light to indicate when brakes need replacement. However, this trouble light is present to monitor the hydraulic braking system through brake fluid pressure and does not monitor brake pad wear. A squeal from the brakes may be a warning, or may indicate that the rivets holding the brakepad to its backing are contacting a rotor or drum which can cause scoring of the rotor or drum. Should the pad be totally worn out, the noise would be from the pad backing contacting the rotor or drum, which would cause considerable damage to the rotor or drum.

Another article which is prone to wear is a tire for use on an automobile, truck, or aircraft landing gear, for example. Tires wear as a result of frictional contact with road surfaces. Furthermore, tires are prone to other problems in connection with pressure and temperature. An improperly inflated tire or worn tire may be manifested as reduced efficiency in gas mileage, reduced performance in ride and handling, reduced performance in vehicle braking, reduced cornering ability, and potential blowout or other catastrophic failure.

Another article that is prone to wearing are bearings. Bearings are the number one cause of motor failure (42%). Some of these failures are due to excessive wear due to heavy loading or incorrect loading (e.g., thrust loading on deep groove ball bearings).

Mechanical contact seals are also prone to wearing. Mechanical contact seals are in widespread use in a wide variety of rotating machinery including pumps, motors and other actuators. The range of applications includes industrial, aircraft, marine, nuclear, and automotive to name a few. Many of these applications are critical and involve sealing lubricating fluids, contaminated air, process fluids, and explosive materials such as hydrocarbon-based fluids. The reliability and lifetime of seals represent recurrent problems which are frequently experienced and well-recognized in industry. For example, motor-pumps are probably the most prevalent critical industrial application of motors. It is generally known that the most frequent cause of failure are the pump seals. Some pump manufacturers have employed more costly magnetic couplings to avoid the problems associated with seal failures. Significant research and development is occurring to provide long-life, reliable seals.

However, there is presently no system which monitors the integrity of seals other than external, machinery-mounted sensors.

Additionally, conventional techniques for monitoring pressure and temperature information relating to an article and/or an environment such as, for example, in a carbon brush or pump chamber often prove to be expensive and/or cumbersome.

In view of the above, there is a strong need in the art for an improved apparatus, system and/or method for determining wear and the rate of wear of an article such as a seal, a bearing, a carbon brush, brake pad or tire, for example. Furthermore, it would be highly desirable to have such an apparatus, system and/or method which can also determine pressure and/or temperature information relating to the article.

SUMMARY OF THE INVENTION

The present invention employs an optical fiber to facilitate the measure of wear and the rate of wear of an article that the optical fiber is embedded in. By embedding at least one optical fiber into the article, information relating to the wear and rate of wear of the article can be obtained. For example, in the case of a carbon brush of a dynamoelectric machine, an optical fiber is embedded into the carbon brush in order to obtain such wear data. As the article (i.e., carbon brush) wears so does the optical fiber which has its length direction disposed substantially parallel to the direction of wear of the article.

A light beam is directed into one end of the optical fiber and the light is transmitted through the optical fiber to the surface at the end of the fiber which the brush is in contact with. The light is reflected off the worn surface at the commutator and transmitted back through the optical fiber. The present invention employs interferometric techniques to analyze the transmitted light signal (i.e., measurement signal) and a reference signal. From the interferometric techniques, information relating to the wear and rate of wear of the fiber optic cable can be determined. Since the optical fiber is substantially weaker than the article it is disposed in, the wear and rate of wear of the optical fiber is substantially that of the article. Thus, wear and rate of wear of the article can be conveniently determined. Wear and rate of wear may be determined extremely accurately with a precision of a fraction (e.g. $1/10$) of the wavelength of the transmitted light beam. Furthermore, most dynamoelectric machines employ a multitude of brushes (perhaps 8 or more). The present invention affords for sharing a common light source and some sensing and analysis devices.

The aforementioned technique may be employed to analyze wear and rate of wear of a variety of articles including brake pads and tires. For example, an optical fiber may be embedded in a brake pad such that as the brake pad wears so does the optical fiber in its length direction. By using interferometric techniques as discussed herein, the amount of wear and the rate of wear of the brake pad can be determined. Likewise, the amount of wear and the rate of wear of a tire can be determined employing a similar technique. Furthermore, the rate of wear of bearings in a motor and seals in a pump can be detected by embedding optical fibers in the bearings and seals. The optical fibers can be used to detect wear in other technologies, such as semiconductor fabrication and the wear in polishing and buffing pads used in semiconductor fabrication and other applications.

Additionally, the present invention provides for determining other information such as that relating to surface assessment, article related temperature and/or pressure, motor speed, contaminants, and article related pressure and/or environmental related pressure.

Light reflected off a surface of something the article is in contact with will have encoded therein data relating to the condition of the surface. Thus, if the article is in contact with a commutator surface for example, the light will also be reflected off the surface of the commutator and will change in intensity relative to the passing of the commutator bars and slots and to the condition of the commutator surface. This change in light intensity can be used in accordance with the present invention to determine the condition of the commutator surface (which tend to exhibit changes in reflectivity which correlates to various operational material, and environmental problems).

Additionally, an optical fiber having a temperature-sensitive index of refraction may be used in accordance with the present invention to determine change in temperature of an article and/or the environment. A change in the index of refraction due to a temperature change will cause a shift in a peak transmission/reflection wavelength of the light being reflected back off the surface. Temperature estimates of the medium (e.g., article body or environment) surrounding the optical fiber may be made by analyzing the attenuation of the reflected light signal at specific wavelengths.

Furthermore, the present invention may be employed to determine the speed of a motor. Time-based frequency measurements of the reflected light beam pulses off the discrete, reflective commutator bar surfaces may be employed to provide indication of motor speed.

The present invention may also be used to determine pressure information. An optical fiber with an embedded grating structure such as a Bragg grating, will undergo micro-bending as a result of pressure applied thereto. The affect of this bending is the shift in wavelength and intensity of the reflected light signal, which varies in relation to the amount of deformation of the optical fiber. Accordingly, the optical fiber can be employed to provide pressure data relating to an article/medium it is exposed to. For instance, if the optical fiber is embedded in an article such as a carbon brush, the optical fiber can provide data relating to the pressure the carbon brush is exposed to. Similarly, if the optical fiber is placed in an environment such as a pump chamber, the optical fiber can provide data relating to the pressure within the pump chamber. Additionally, by exposing the optical fiber to the interior of a tire, for example, pressure information relating to the inflation of the tire may be obtained.

In one aspect of the present invention, an optical fiber is embedded in a conventional mechanical seal and a light source is introduced into the fiber. The fiber type, fiber orientation, fixturing, and doping of the waveguide can determine the parameters which may be measured. Multiple parameters can be measured using one or more embedded fibers. Doping of the fiber can enable seal temperature and fluid temperature measuring. Similarly the characteristics of the lubricating film can be measured, such as the thickness, film variation over time, fluid advancement rate and geometry, contaminants and potentially cavitation. A series of parallel waveguides may also monitor the advancing edge of the fluid film as the seal wears. A group of fibers may also image the rotating metal shaft through the lubricating film to detect signs of shaft wear. A bragg grating in the embedded fiber may also provide information regarding seal compression, thermal expansion, or deformation of the seal.

In accordance with one specific aspect of the present invention, a system for determining wear of an article is provided and includes: an optical fiber for transmitting light from a light source, the optical fiber being embedded in the article; and an interferometric system operatively coupled to the optical fiber and a processor; wherein the interferometric system provides the processor with information relating to wear of the optical fiber, and the processor determines wear of the article and rate of wear based on the information.

According to another aspect of the present invention, a system for determining wear of an article is provided and includes: a light source for generating a primary beam; a beam splitter for receiving the primary beam and splitting the primary beam into a reference beam and a measuring beam, the beam splitter directing the reference beam to a mirror; an optical fiber at least part of which is embedded in the article, the optical fiber having first and second ends, the first end receiving the measuring beam, the second end being flush with a contacting surface of the article, the article being in contact with a surface; and a detector for detecting an interference beam from the beam splitter, the interference beam comprising a reflected reference beam and a reflected measuring beam, the detector transforming the interference beam into an electrical signal; and a processor for receiving the electrical signal, the processor determining wear and rate of wear of the article based on the electrical signal.

Another aspect of the present invention provides for a system for determining temperature related information of an article which includes: an optical fiber for transmitting light from a light source, the optical fiber being embedded in the article, the optical fiber having a temperature-sensitive doping applied, and being operatively coupled to a temperature sensor, the temperature sensor being adapted to receive at least a portion of a measuring beam being transmitted through the optical fiber, the temperature sensor being operatively coupled to a processor, the temperature sensor providing the processor with data based on the measuring beam, and the processor determining temperature related information based on the data.

Still another aspect of the present invention provides for a system for determining pressure of an article which includes: an optical fiber for transmitting light from a light source, the optical fiber being embedded in the article, the optical fiber having at least one induced microbend, and being operatively coupled to a pressure sensor, the pressure sensor being adapted to receive at least a portion of a measuring beam being transmitted through the optical fiber, the pressure sensor being operatively coupled to a processor, the pressure sensor providing the processor with data based on the measuring beam, and the processor determining pressure related information based on the data.

Another aspect of the present invention provides for a carbon brush for providing current to a commutator of a dynamoelectric machine, the carbon brush having at least one optical fiber embedded therein.

In accordance with another aspect of the present invention, a method for determining wear is provided and includes the steps of: using an article having an optical fiber embedded therein; using an interferometric system operatively connected to the optical fiber to collect information relating to the optical fiber; and using a processor operatively coupled to the interferometric system to determine wear and rate of wear of the article based on the information.

Still yet another aspect of the present invention provides for a system for determining a condition of an object (e.g., abraded surface, corrosion, contaminants, scorching) which includes: an optical fiber for transmitting a measuring light beam toward the object and for transmitting at least a portion of the measuring light beam reflected back from the object; a signal monitor operatively coupled to the optical fiber and a processor, the signal monitor adapted to receive the reflected measuring light beam; wherein the signal monitor provides the processor with information based on the reflected measuring light beam, and the processor determines a condition of the object from the information.

In yet another aspect of the present invention provides a system for determining at least one condition of a bearing (e.g., deep groove ball bearing, sleeve bearing). The system comprises at least one optical fiber embedded in a bearing. The at least one optical fiber is adapted to transmit light from a light source. The system also comprises an interferometric system operatively coupled to the optical fiber and a processor, wherein the interferometric system provides the processor with information relating to at least condition of the bearing, and the processor determines a state of at least one condition of the bearing based on the information.

Another aspect of the invention relates to a system for determining at least one condition of a bearing. The system comprises a light source for generating a beam of light and at least one optical fiber at least part of which is embedded in a bearing. The at least one optical fiber includes first and second ends. The first end receives the beam of light. The second end is flush with a contacting surface of the bearing. The system also comprises a measuring system operatively coupled to the optical fiber, wherein the optical fiber provides the measuring system with information relating to the at least one condition of the bearing.

In yet another aspect of the invention provides for a method for determining at least one condition of a bearing. The method comprises the steps of providing a bearing having an optical fiber embedded therein, using a measuring system operatively connected to the optical fiber to collect information relating to the optical fiber and using a processor operatively coupled to the measuring system to determine the at least one condition of the bearing based on the information.

In yet another aspect of the invention relates to a system for determining the amount of material removed in a semiconductor process. The system comprises a light source for generating a beam of light, at least one optical fiber at least part of which is embedded in a semiconductor device, the at least one optical fiber having first and second ends, the first end receiving the beam of light, the second end being flush with a contacting surface of the semiconductor device and a measuring system operatively coupled to the optical fiber. The optical fiber provides the measuring system with information relating to an amount of material removed from the semiconductor device.

Another aspect of the invention relates to a system for determining wear of a polishing pad. The system comprises at least one optical fiber embedded in a polishing pad, the at least one optical fiber being adapted to transmit light from a light source and an interferometric system operatively coupled to the optical fiber and a processor. The interferometric system provides the processor with information relating to wear of the polishing pad and the processor determines a state of the polishing pad based on the information and surface finish, smoothness, color & reflectance.

Yet another aspect of the invention relates to a system for determining at least one condition of a seal. The system comprises at least one optical fiber embedded in a seal, the at least one optical fiber being adapted to transmit light from a light source and an interferometric system operatively coupled to the optical fiber and a processor. The interferometric system provides the processor with information relating to at least one condition of the seal, and the processor determines a state of the at least one condition of the seal based on the information.

In another aspect of the invention, a system is provided for determining at least one condition of a seal. The system comprises a light source for generating a beam of light, at least one optical fiber at least part of which is embedded in a seal, the at least one optical fiber having first and second ends, the first end receiving the beam of light, the second end being flush with a contacting surface of the seal and a measuring system operatively coupled to the optical fiber. The optical fiber provides the measuring system with information relating to the at least one condition of the seal.

Another aspect of the invention relates to a method for determining at least one condition of a seal. The method comprises the steps of providing a seal having an optical fiber embedded therein, using a measuring system operatively connected to the optical fiber to collect information relating to the seal and using a processor operatively coupled to the measuring system to determine the at least one condition of the seal based on the information.

A system for controlling pressure of a seal against a contact surface is provided. The system comprises at least one optical fiber embedded in a seal, the at least one optical fiber being adapted to transmit light from a light source, a measuring system operatively coupled to the optical fiber, the optical fiber providing the measuring system with information relating to at least one condition of the seal, and at least one piezoelectric device embedded in the seal, the at least one piezoelectric device being operatively coupled to a variable voltage source. The measuring system varies the voltage of the voltage source based on the information relating to the at least one condition of the seal causing the at least one piezoelectric device to flex and vary the seal pressure against the contact surface.

Yet another aspect of the invention relates to a fluid pressure control system. The fluid pressure control system comprises a seal disposed between a first chamber and a second chamber, at least one optical fiber embedded in the seal, the at least one optical fiber being adapted to transmit light from a light source, a measuring system operatively coupled to the optical fiber, the optical fiber providing the measuring system with pressure information relating to at least one of the first chamber and the second chamber, and a piezoelectric device embedded along a substantial portion of the seal, the at least one piezoelectric device being operatively coupled to a variable voltage source. The measuring system varies the voltage of the voltage source based on the pressure information causing the at least one piezoelectric device to flex and vary the seal contact pressure within at least one of the first and the second chamber.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 8 is a representative lookup table which provides for narrowing down the possible causes for the wear/damage to a commutator surface in accordance with the present invention;

FIG. 19 is a partial schematic diagram illustrating an alternate control system according to the present invention for controlling fluid pressure.

DESCRIPTION OF THE PREFERRED EMBODIMENTS

Figure 1:
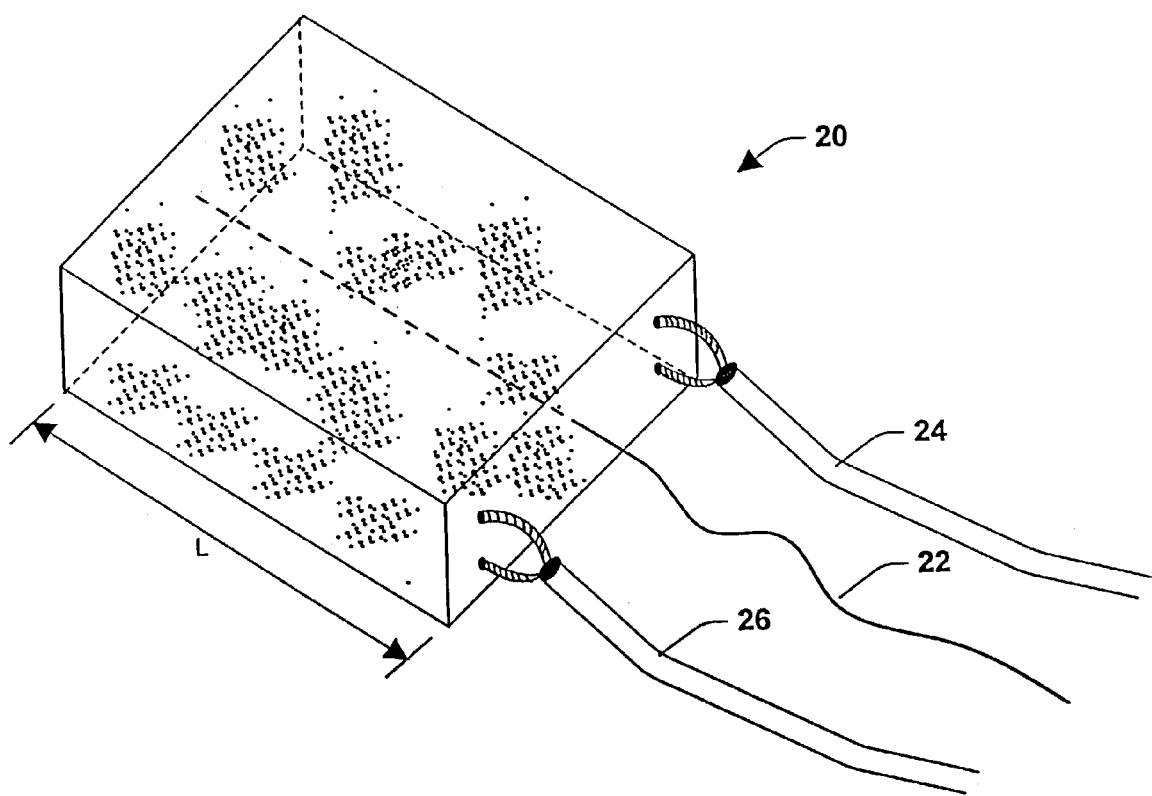
FIG. 1 is a perspective view of a carbon brush having an optical fiber embedded therein in accordance with the present invention.

The present invention will now be described with reference to the drawings, wherein like reference numerals are used to refer to like elements throughout.

As is mentioned above, the present invention employs an optical fiber to provide data relating to an article the fiber is embedded in or data relating to an environment the fiber is exposed to. Such data includes the amount of wear and the rate of wear of the article. Furthermore, the present invention can provide data relating to surface condition assessment, article temperature and/or environment temperature, motor speed, and article pressure and/or environmental pressure.

Referring initially to FIG. 1, a carbon brush 20 is shown in perspective view with an optical fiber 22 embedded therein. Two current carrying conductors 24, 26 are shown fixed to a non-contacting end of the carbon brush. The other end of the carbon brush 20 slidably contacts with another surface (e.g., commutator surface) which is not shown. The current carrying conductors 24, 26 supply current to the carbon brush 20 which is transferred by the electrically conductive carbon brush 20 to a commutator 30 (FIG. 2) of a dynamoelectric machine (e.g., motor). As will be shown in greater detail below, a spring biases the brush 20 against the commutator 30 thereby forming a sliding contact. Electrical power is then conducted from the carbon brush 20 through the sliding contact to the commutator 30. A particular motor system may have one or more brush assemblies—each assembly typically including a housing that slidably receives two or more electrical brushes.

Carbon brushes are normally composed of a carbon based matrix. There are a variety of brush compounds for a variety of applications. There are five basic categories of brushes: carbon, carbon-graphite, electrographite, graphite, and metal-graphite. The term "carbon" has a broad meaning that refers to any brush having any quantity of carbon in it regardless of the quantity of other materials. The term also has a narrower meaning to refer to a brush predominantly composed of amorphous carbon such as petroleum coke. Carbon-graphite refers to a brush composed of a mixture of carbon (as defined above) and graphite. Electrographite refers to a brush composed of carbon subjected to intense heat in an electric furnace that graphitizes the carbonaceous binder. Graphite refers to a brush that is predominantly graphite mined from the ground or manufactured in an electric furnace. Metal-graphite refers to graphite brushes having a quantity of metal such as silver or copper.

It is to be appreciated that any type of brush suitable for carrying out the present invention may be employed and falls within the scope of the present invention. Such brushes have widescale application in DC motors, senevators, and slip rings to name a few. Furthermore, it is to be understood that the present invention is not limited to application in brushes. Rather, the present invention may be employed in conjunction with almost any type of article or device that is prone to wear. Moreover, although only one optical fiber 22 is shown embedded in the article 20, it is to be appreciated that more than one optical fiber 22 may be embedded in the article 20 to obtain wear and rate of wear data relating to different parts of the article 20.

As can be seen in FIG. 1, the optical fiber 22 is embedded in the carbon brush 20. The optical fiber 22 is embedded such that its length direction is substantially parallel to the direction of wear of the carbon brush 20. Thus, as the carbon brush 20 wears over time due to sliding contact with the commutator 30 (FIG. 2), the end of the optical fiber will similarly wear and the length of the optical fiber decreases. Since the optical fiber 22 is substantially weaker than the surrounding contacting surface area of the carbon brush 20, the optical fiber 22 wears substantially at the same amount and rate as the carbon brush 20 which the optical fiber 22 is embedded in.

In order to embed the optical fiber 22 in the carbon brush 20, a small cylindrical channel is drilled through the body of the carbon brush. The diameter of the channel being slightly larger than the diameter of the optical fiber. The optical fiber 22 is strung through the brush 20 so as to be taut within the channel. The fiber optic cable 22 may be secured within the channel with an epoxy type material. Fast curing epoxies (such as Devcon 5 Minute Epoxy) or adhesives that cure quickly when exposed to ultra-violet light (such as Norland 61) may be useful in some applications, and may be utilized to manufacture at least one specific aspect of the present invention. Any type of epoxy, glue or other means suitable for securing the fiber optic cable 22 within the channel may be employed as long as it does not exceed the hardness of the brush, does not contaminate the brush, fiber, or commutator, and does not score or mark the commutator 30. The optical fiber 22 is cut so as to be flush with the surface of the carbon brush that comes into contact with the commutator surface.

Figure 2:
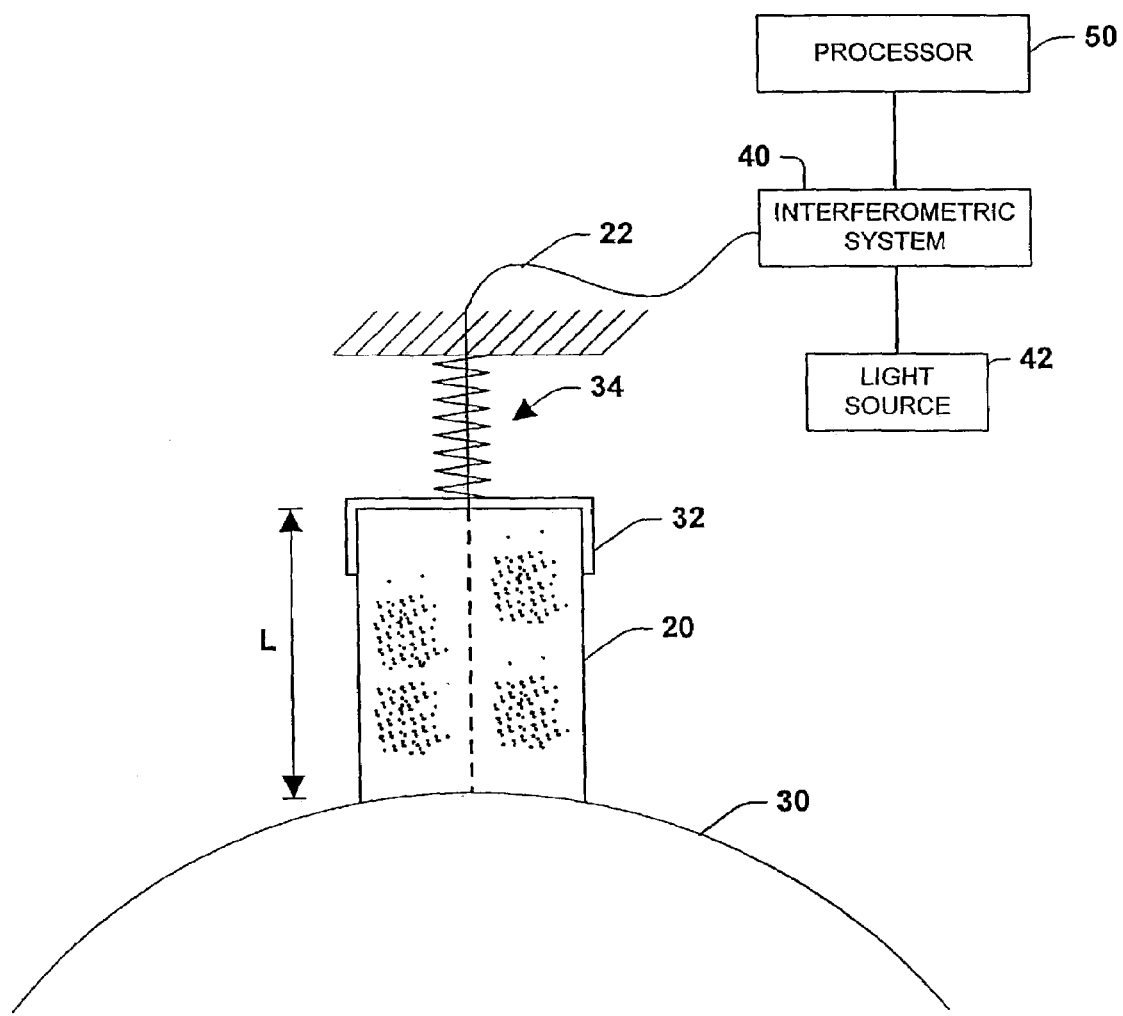
FIG. 2 is a is a functional schematic diagram of the integrated carbon brush and optical fiber in accordance with the present invention.

FIG. 2 is a is a functional schematic diagram of the integrated carbon brush 20 and optical fiber 22 in accordance with the present invention. The carbon brush 20 is shown held by a carbon brush holder 32. The carbon brush 22 is shown contacting a commutator 30 of a DC motor. The carbon brush 20 is biased against the surface of the commutator 30 by a spring follower 34 (e.g., compression spring). The spring follower 34 (which is operatively connected to an outside surface of the brush holder 32) urges the carbon brush 20 toward the commutator 30 so that the commutator-side end portion of the carbon brush 20 is pressed on the outer peripheral surface of the commutator 30. It will be appreciated that any suitable biasing means for urging the carbon brush 20 toward the commutator 30 may be employed. Accordingly, the spring follower 34 may be replaced with a torsion spring, a leaf spring, a glass-shaped spring or the like. The brush holder 32 holding the carbon brush 20 and spring follower 34 is made of a metallic material such as brass, stainless steel or the like and is suitable for firmly securing the carbon brush 20 in a relatively static position with respect to a direction normal to the commutator surface.

The optical fiber 22 is shown embedded in the carbon brush 20 such that one end is exposed to the commutator surface 30. The other end of the optical fiber 22 is shown operatively coupled to an interferometric system 40 which is discussed in greater detail below. The interferometric system 40 is operatively coupled to a light source 42 and a processor 50. It is to be appreciated that the interferometric system 40 and light source 42 could be integrated and even attached to the end of the carbon brush 20 away from the commutator 30. Furthermore, the interferometric system may include a wireless transceiver for wirelessly transmitting data to the processor 50.

As the carbon brush 20 is used it will wear due to electrical, chemical, and mechanical characteristics as a result of contact with rotating the commutator surface. The spring follower 34 provides for continual contact between the carbon brush 20 and commutator 30. Thus, as the carbon brush wears 20, the length of the carbon brush 20 decreases and the carbon brush holder 32 becomes closer in proximity to the commutator surface. The length "L" of the optical fiber 22 will likewise wear as the length of the carbon brush 20 wears. However, the end of the optical fiber that is flush with the contacting surface of the carbon brush 20 will be in like proximity (of the carbon brush 20) to the commutator surface as a result of the optical fiber 22 being embedded in the carbon brush 20. Through interferometric techniques discussed in greater detail below, the amount of wear and rate of wear of the optical fiber 22 can be determined. Since the optical fiber 22 wears as a function of the wear of the brush 20, the interferometric techniques provide for very accurately determining the amount of wear and rate of wear of the carbon brush 20.

Figure 3:
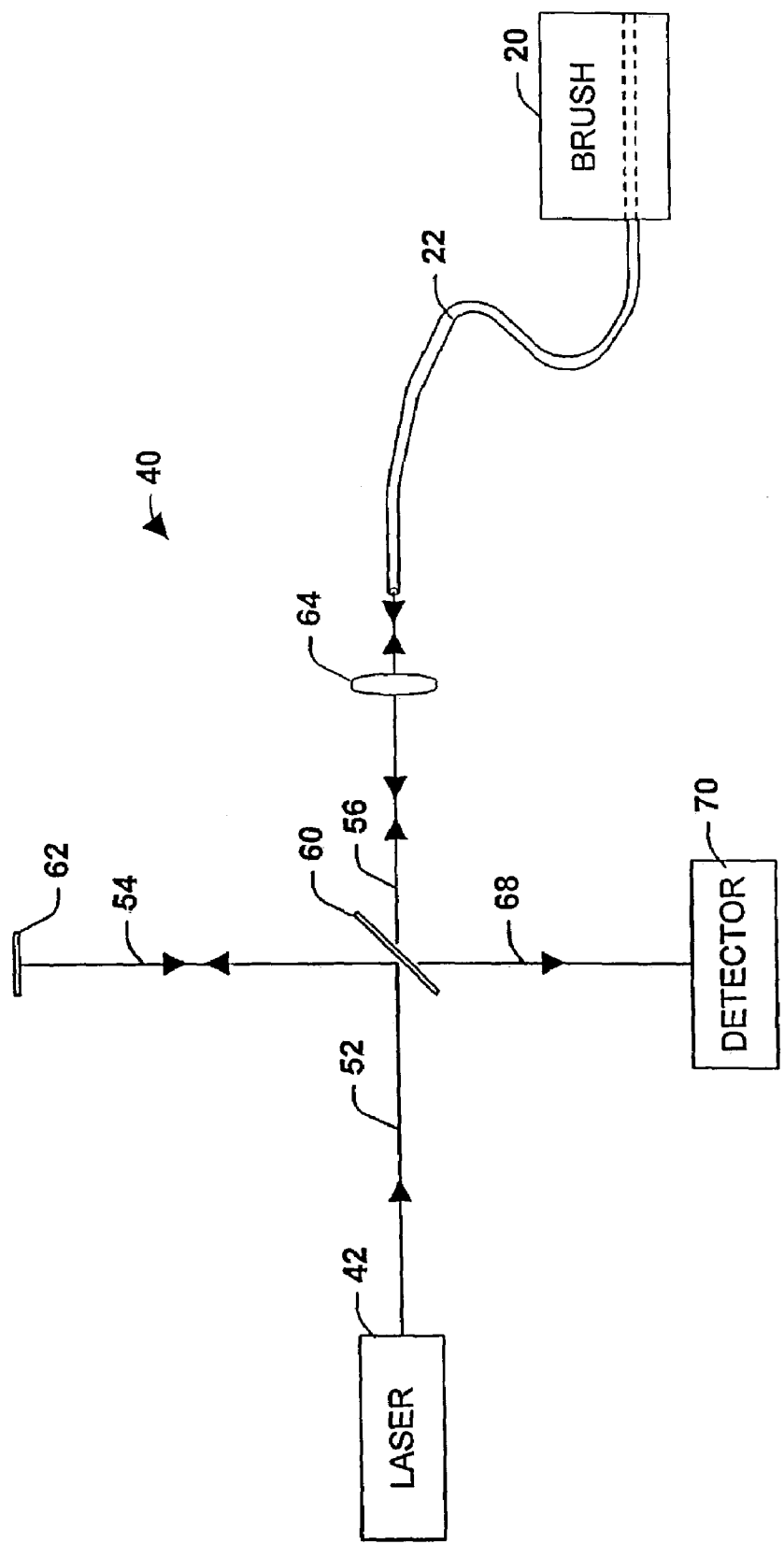
FIG. 3, a schematic diagram of an interferometric system in accordance with the present invention.

Turning now to FIG. 3, a schematic diagram of the interferometric system 40 is shown. The interferometric system 40 is employed in determining the reduction in length of the optical fiber 22 which in turn represents the amount of wear of the carbon brush 20.

One specific aspect of the present invention employs a Michelson-type interferometer. In this kind of interferometer, a light beam 52 from a coherent light source 42 such as a laser is split into two beams using a beam splitter, one of which can be referred to as a reference light beam 54 and the other as a measuring light beam 56. A semireflective mirror 60 is disposed in the path of the light beam 52 at an angle of 45E and is used as the beam splitter. A cube formed by cementing two prisms together may also be used as the beam splitter 60, where the cemented surface is disposed in the beam path at a 45E angle.

When the light beam 52 from the light source 42 (e.g., laser) reaches the beam splitter 60, the light beam 52 is split into the reference beam 54 and the measuring beam 56. The reference beam 54 is reflected toward a mirror 62 where it is reflected back toward the beam splitter 60. The measuring beam passes through the beam splitter 60 towards a focus lens 64. The focus lens 64 focuses the measuring beam 56 to enter a free end of the optical fiber 22. The measuring beam 56 travels through the optical fiber 22 toward the portion of which is embedded in the brush 20. The measuring beam 56 is incident on an interface between the end of the optical fiber 22 and the commutator surface. The commutator surface, typically being reflective, causes the measuring beam 56 to be reflected back away from the interface towards the beam splitter 60 through the same optical fiber 22. The reflected reference beam 54 and reflected measuring beam 56 are combined by the beam splitter 60 to form an interference beam 68 which is directed toward optical detector 70.

Depending on the phasing of the two beams 54, 56.with respect to one another, the interference beam 68 can assume an amplitude between the sum of the individual amplitudes of the two beams 54, 56 (constructive interference) and zero (destructive interference). When the two beams 54, 56 are 180E out of phase (i.e., destructive interference), a completely dark fringe results. When the two beams 54, 56 are in phase, a bright fringe results. The light being preferably of laser form is a standing wave pattern. Accordingly, each fringe (e.g., dark fringe or portion thereof) as detected by a detector 70 corresponds to a reduction in the length of the optical fiber 22 of 2λ (i.e., 2 the wavelength of the light source 42).

Thus, by counting the number of fringe changes observed on the output of the detector 70, the reduction in the length of the optical fiber 22 can be determined with great precision since the source beam 52 is typically of high frequency and short wavelength (2). For instance, if the reference beam is from a laser diode having an emission wavelength of 800 nm, one dark fringe represents a reduction in length of the optical fiber 22 of 400 nm. In addition, the signal from detector 70 typically provides grayscale information rather than just binary information indicating bright fringe (1) or dark fringe (0). As a result, the range of intensity values provided by detector 70 allows processor 50 to determine intermediate fringe values. Through well known techniques such as interpolation, the processor may readily determine fringe intensity values such as 70% dark fringe. Intermediate fringe values can easily be determined up to $\frac{1}{10}$ the range of bright-dark intensity values. This permits determining the change in length of optical fiber 22 and carbon brush 20 by $\frac{1}{10}$ of 400 nm if an 800 nm light source is used. In this example, the change in brush length of 40 nm can be readily detected. The reduction in length of the fiber optic cable 22 by 400 nm equates to a corresponding reduction in length of the carbon brush 20 by 400 nm. Since the carbon brush 20 is substantially hard in composition and may take many months for it to wear only 1 inch, determining the amount of wear at such a micro-level (e.g., in nanometers) is useful.

Furthermore, since the amount of wear can be determined at the micro-level, the present invention provides for the prompt determination of the rate of wear of the carbon brush 20. More particularly, by monitoring the amount of wear of the carbon brush 20 over time a determination as to the rate of wear of the carbon brush 20 can be made. Such monitoring can be made by a processor 80 (FIG. 4a) employing a clock (not shown). As a result of determining the rate of wear, the processor 80 can forecast when the carbon brush 20 will need to be replaced. Precise amount of wear information enables precise rate of wear information to be determined in a very short time. Early indication of wear problems are provided in hours or days rather than weeks or months. This permits early identification of the cause of wear problems and fault correction before brushes wear excessively or machinery damage occurs. It is also possible to correlate abnormal wear problems directly with operational and environmental changes. Accordingly, the present invention affords for scheduled maintenance of articles prone to wear which greatly facilitates maximizing article usage and minimizes process down time. In other words, if the rate of wear of the article was not determinable a user could not forecast an optimal time for replacement of the article. Rather, the user would simply shutdown the process using the article when the amount of wear reached a predetermined level. Typically, machinery is periodically shut down, disassembled, and brushes inspected. The brushes will often be replaced with substantial remaining useful life in order to avoid the risk of unexpected failure and machinery damage. In DC brush-type motors, the brushes are the highest maintenance, most failure prone component. On the other hand, the present invention affords for relatively long-term forecasting of when to replace an article. This aspect of the present invention facilitates process efficiency since shutdowns can be planned in advance.

Figure 4A:
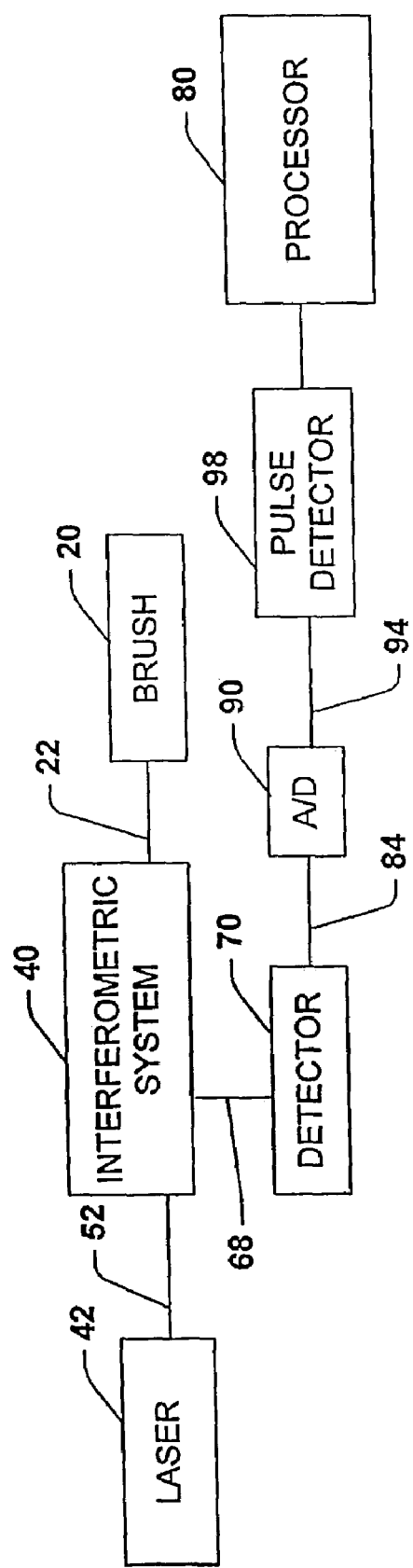
FIG. 4a is a schematic block diagram of one specific system for determining the amount of wear of an article in accordance with the present invention.

FIG. 4a is a schematic block diagram of one specific system for determining the amount of wear of an article in accordance with the present invention. A source of monochromatic light such as a laser 42 provides light to optical fiber 22 of the interferometric system 40. Preferably, the laser 42 is a frequency stabilized laser however it will be appreciated that any laser or other light source (e.g., laser diode or helium neon (HeNe) gas laser) suitable for carrying out the present invention may be employed. The laser 42 outputs a laser beam 52 which is supplied to the optical fiber 22 of the interferometric system. The interferometric system 40 operates in the manner described above to split the beam 52 into two beams (reference light beam 54 and measuring light beam 56). As mentioned above, after traveling over independent paths, the measuring beam 56 and reference beam 54 are recombined to form an interference beam 68.

The interference beam 68 is supplied to detector 70 which converts the interference beam 68 into an electric signal which is a signal having a magnitude and frequency corresponding to a standing wave pattern or fringe pattern of the interference beam 68. As noted above, depending on the phasing of the two beams 54, 56 with respect to one another, the interference beam 68 can assume an amplitude anywhere between the sum of the individual amplitudes (constructive interference) and the difference of the individual amplitudes (destructive interference). When the two beams 54, 56 are 180E out of phase (i.e., destructive interference), a completely dark fringe results. When the two beams 54, 56 are in phase, a bright fringe results.

The detector 70 is preferably a photodetector or the like which outputs an electrical signal the amplitude of which is indicative of the intensity of light received by the detector 70. The electric signal output by the detector 70 is an analog signal which travels along line 84 and is input to analog-to-digital (A/D) converter 90 which digitizes the analog signal for ease of processing. The digital signal output by the A/D converter 90 is input via line 94 to a pulse detector 98. Each dark fringe (or portion thereof) appears as a zero ("0") or low signal in digital form. Each fringe change that results as the interference beam 68 is passed through the detector 70 corresponds to a reduction in the length of the fiber optic cable 22 of $2\lambda$ (i.e., 2 the wavelength of the reference beam 54). The pulse detector 98 monitors the change in fringes and counts each fringe that cycles therethrough. It will be appreciated that any suitable method for determining the number of fringes may be employed to carry out the present invention and falls within the scope of the claims.

The number of fringes counted by the pulse detector 98 is input to processor 80. The processor 80 is programmed to control and operate the various components within the present invention in order to carry out the various functions described herein. The processor or CPU 80 can be any of a plurality of processors, such as the p24T, Pentium 50/75, Pentium 60/90, and Pentium 66/100, Pentium PRO and Pentium 2, and other similar and compatible processors. The manner in which the processor 80 can be programmed to carry out the functions relating to the present invention will be readily apparent to those having ordinary skill in the art based on the description provided herein. The processor 80 counts the number of fringes with respect to a reference fringe starting count. By the number of fringes that have been counted, the processor 80 can readily determine the reduction in length of the optical fiber 22 with great precision since the reference beam 54 is typically of high frequency. In turn, by determining the reduction in the optical fiber 22, the amount of wear of the carbon brush 20 (i.e., article) is determined as well. The rate of wear can be determined via $\Delta$fringe count/time.

It is also possible to determine intermediate fringe values and determine brush wear and rate of wear more accurately than just counting fringes as described above. This is accomplished by utilizing an interpolation module 98a (in FIG. 4b) to analyze the interference pattern 94. Intermediate fringes which relate to the degree of interference between the reference beam and measurement beam may be determined and passed to processor 80. Processor 80 may then establish precisely the wear and rate of wear of brush 20 by at least 1/10 the wavelength of light used.

Figure 4B:
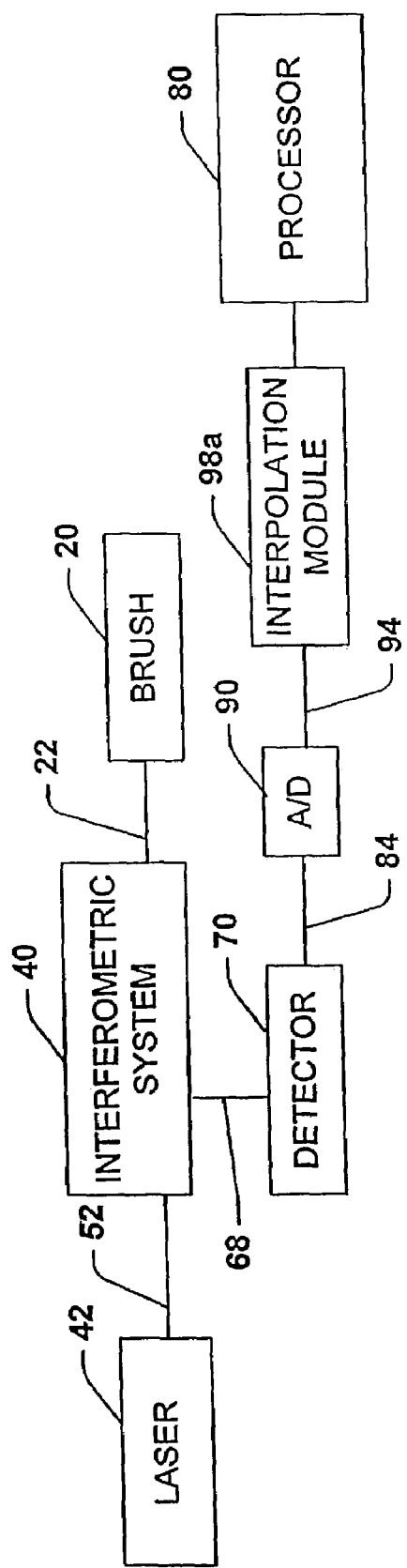
FIG. 4b is a schematic block diagram of an alternate system for determining the amount of wear of an article in accordance with the present invention.
Figure 4C:
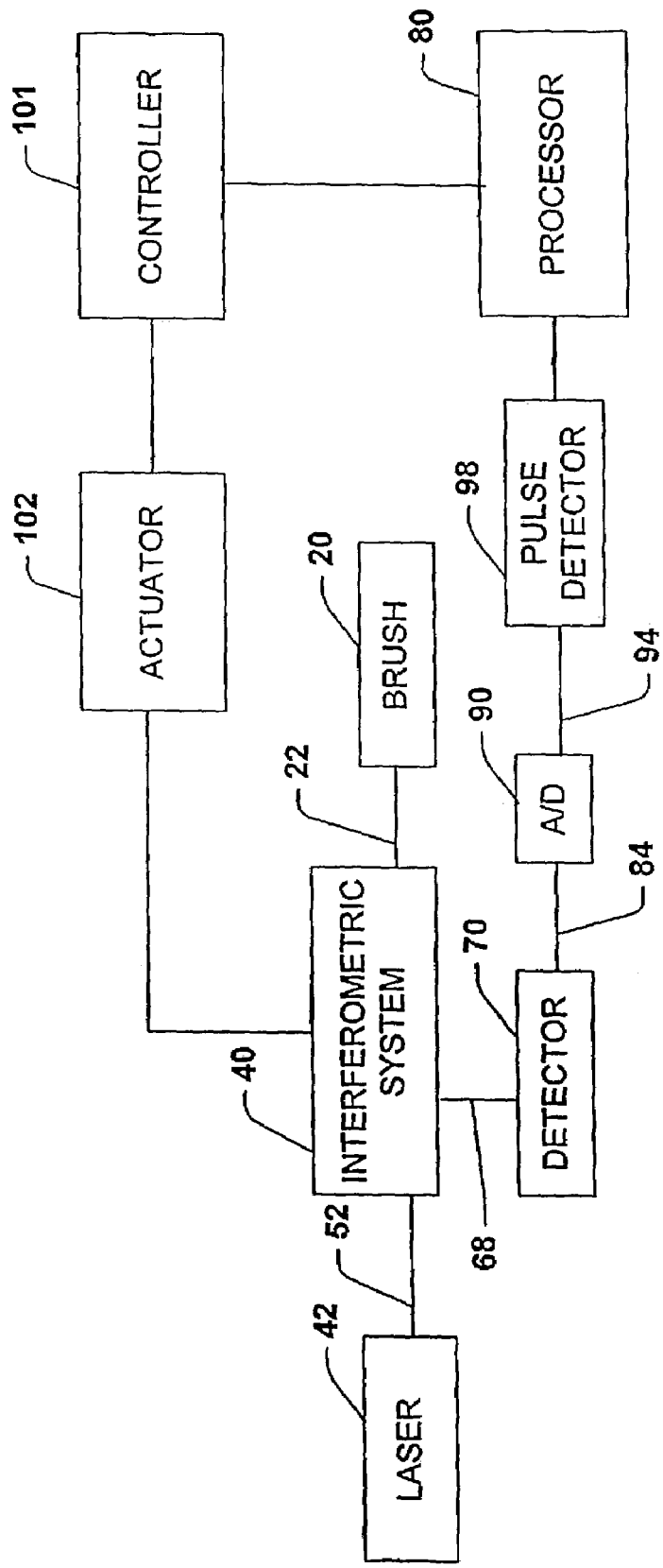
FIG. 4c is a schematic block diagram of yet another alternate system for determining the amount of wear of an article in accordance with the present invention.

An alternative method for implementing the interferometric system is shown in FIG. 4c. Rather than counting or interpolating fringes as previously described, an actuator 102 is coupled to a controller 101. A control signal is output from processor 80 whenever the observed fringe changes intensity. The amount of control action requested my be proportional to the amount of fringe intensity change observed (as in PID controllers) and the direct of control requested is prescribed to return the observed fringe back to it=s original intensity level. The controller 101 takes the commanded change and outputs an appropriate electrical signal, usually a voltage or voltage pulse train to the actuator 102. The actuator 102 is designed to laterally translate the reflective surface 62 receiving the reference beam 54 closer or further from the beam splitter 60. The end result from this closed loop system is that the observed fringe by detector the 70 remains relatively stationary. An amount of displacement of reflective surface 62 required to maintain a stationary fringe pattern directly corresponds to the amount of fiber wear 22 and brush wear 20. A variety of actuators may be used to laterally translate the reflective surface movement such as precision lead screw devices, piezo-electric actuators, and MEMs devices such as a lateral resonator/translator (developed at Case Western Reserve University) or the Scratch Drive Actuator-SDA (developed at UCLA) are candidate actuators.

Figure 5:
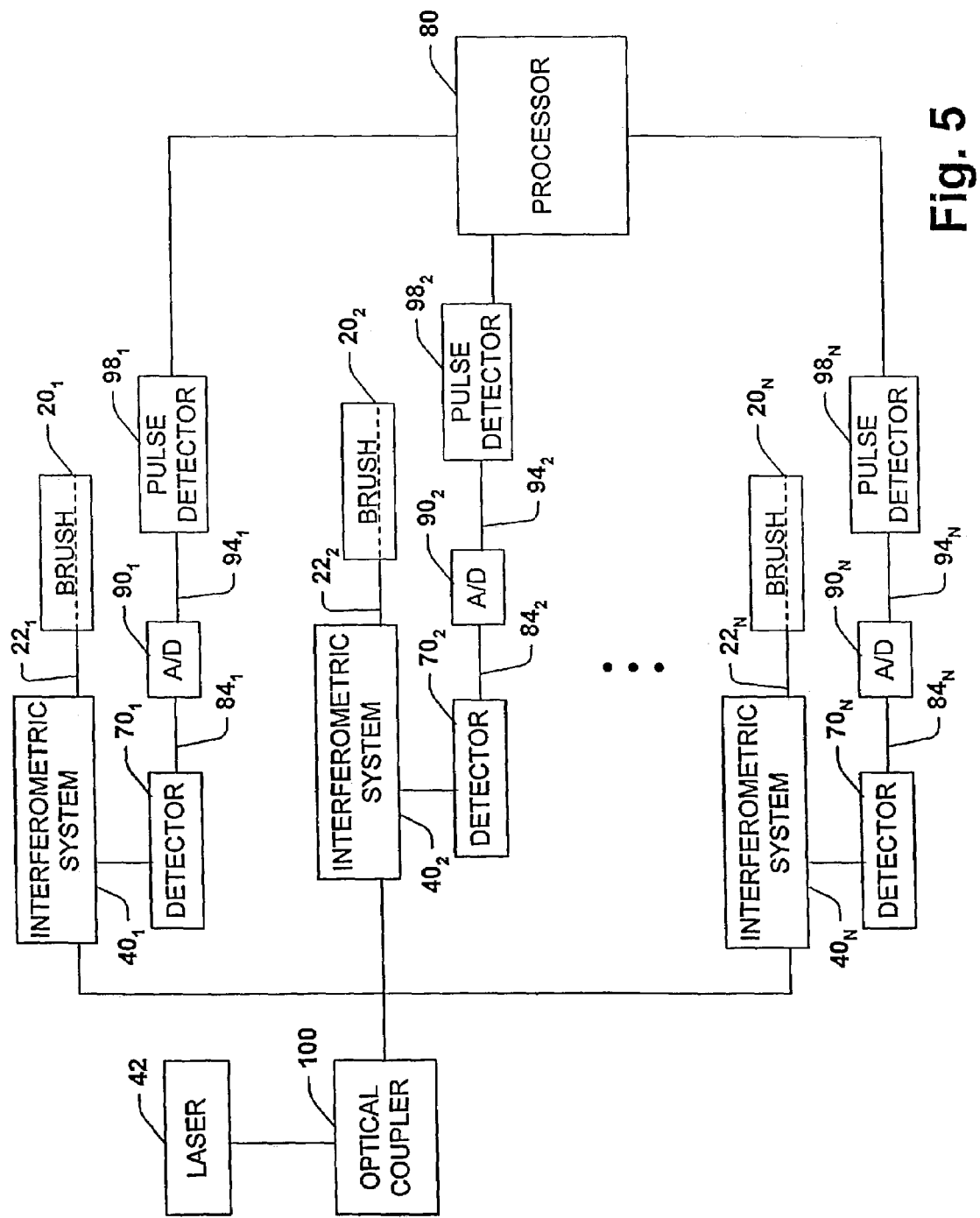
FIG. 5 is a schematic block diagram of another specific aspect of the present invention which provides for the determination of the amount of wear and rate of wear for multiple articles in accordance with the present invention.

FIG. 5 is a schematic block diagram of another specific aspect of the present invention. This embodiment provides for the determination of the amount of wear and rate of wear for multiple articles 20. Oftentimes, in DC motor applications more than one brush is employed to provide current to the motor. The number of brushes used corresponds to the number of poles of the motor. Thus, for example, a six-pole motor would have six brushes. In this embodiment, a plurality of interferometric systems 40 similar to that of FIG. 4a are employed. According to this aspect of the present invention, the amount of wear and rate of wear of N number of articles (i.e., brushes 20) can be determined. Like reference numerals indicate like parts with respect to FIG. 4a and thus further description of these components is not presented for sake of brevity. In order to provide light to the plurality of interferometric systems 40, the laser 42 is operatively connected to an optical coupler 100. The optical coupler 100 couples or splits the laser beam delivered by the laser 42 into multiple outgoing beams for use in the respective interferometric systems 40. The beam emitted from laser 42 is collimated and split into multiple beam portions for introduction into the respective multiple outgoing optical fibers 22. Each split beam portion is introduced into its respective interferometric system 40 in accordance with specific beam introduction criteria.

The present embodiment maximizes the utilization of the laser 42. Frequency stabilized lasers are relatively expensive at the present time and thus maximizing use of the laser 42 is desirable. In broadest terms, this requires making the laser generated beam available to as many functions as possible. A second design objective synergistic with the objective of maximizing laser utilization is to maximize the system's flexibility to deliver the laser beam to the multiple, spatially located brushes 20 which surround the commutator 30. Thus, this specific embodiment of the present invention provides for increased flexibility by splitting the laser beam and delivering the split beam portions through different multiple optical fibers 22 each of which are embedded in different brushes 20.

Each pulse counter 98 of the respective interferometric systems 40 counts the number of digital low signals which correspond to fringes that are cycled through the respective detectors 70 and provides that count to the processor 80. Accordingly, the processor 80 can determine the degree of wear and the rate of wear of each brush 20. It is to be appreciated that the processor 80 may employ any suitable technique (e.g., multi-channel, encoding, multiplexing, etc.) for distinguishing the respective data output by the various pulse detectors 98. It will be appreciated that multi-element detectors 70 and/or a multiplexed A/D 90 could be employed to further consolidate the present embodiment.

It may also be appreciated that the pulse detector 98 may be replaced with corresponding interpolation modules (as shown in FIG. 4b). Alternatively, the system of FIG. 5 can employ a single source, interferometric system, detector and processor by optically switching among the various fibers 22 embedded in brushes to be monitored. An optical switch (not shown) of the type generally known such as mechanically movable reflectors such as prismatic devices or of the electro-optic type such as Lithium Niobate. Either of these techniques will be feasible since we do not need to measure multiple brushes concurrently and the switching time to index to successive brushes is not critical. This latter design provides maximum re-usability of all system components except the brushes and their embedded fiber which must be kept separate.

Figure 6A:
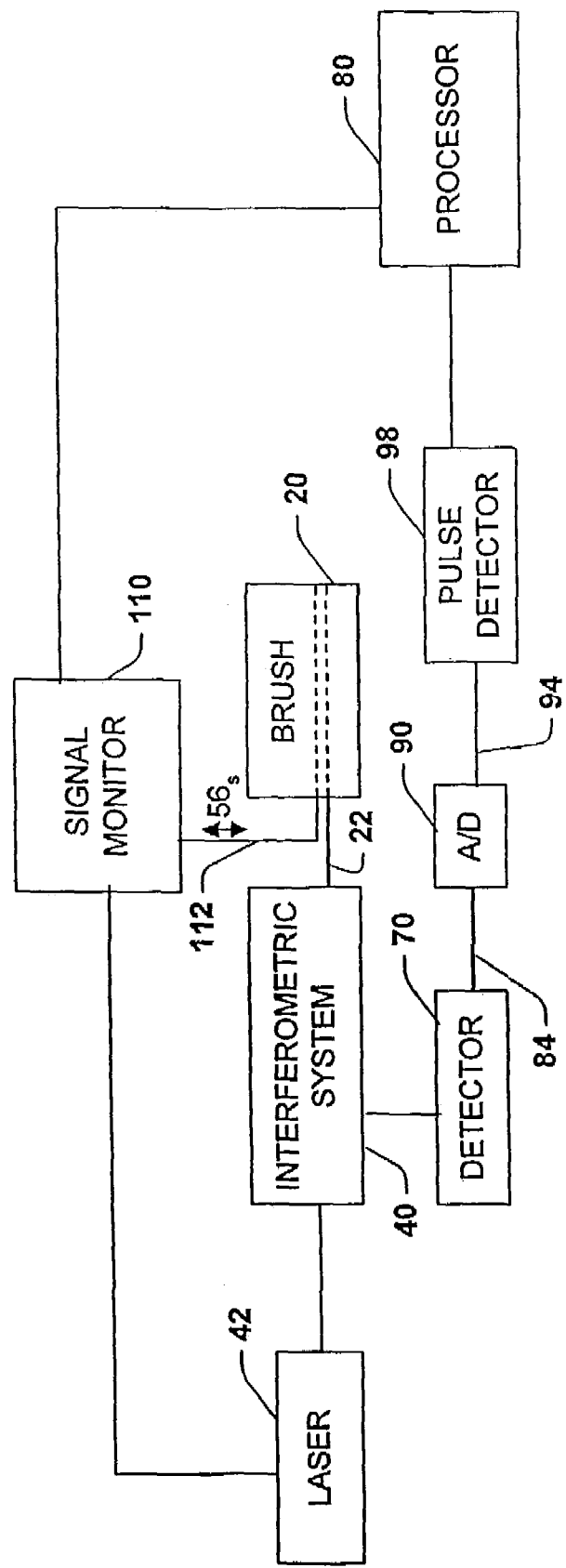
FIG. 6a is a schematic block diagram of another specific aspect of the present invention which affords for surface assessment in accordance with the present invention.

FIG. 6a is a schematic block diagram of another specific aspect of the present invention. This embodiment is similar to that of FIG. 4a but further includes a signal monitor (SM) 110. Like reference numerals between FIGS. 4a, 5 and 6a indicate like parts and thus further discussion related thereto is eliminated in order to avoid redundancy. The SM 110 is operatively coupled to an optical fiber 112, laser 42 and the processor 80. The SM provides for directing a measuring beam $56_s$ from the laser 42 to the optical fiber 112. The measuring beam $56_s$ travels through the optical fiber, at least a portion of which is embedded in an article such as brush 20. The measuring beam $56_s$ will strike an object that the article 20 is in contact with and be reflected back through the optical fiber 112. The SM 110 receives the reflected measuring beam $56_s$. The SM 110 converts the reflected measuring beam $56_s$ to an electrical signal and filters the signal such that a predetermined bandwidth is output to the processor 80. The processor 80 analyzes the signal output by the SM 110 and is able to render an assessment of the condition of the commutator surface from the signal.

More particularly, worn or damaged commutator surfaces exhibit various characteristics. Pitch bar-marking on the commutator surface is a result from low or burned spots on the commutator surface that equals half or all the number of poles of the motor. Heavy slot bar-marking on the commutator surface is a result of etching of the trailing edge of the commutator bar in relation to the number of conductors per slot. Threading with fine lines on the commutator surface is a result of excessive metal transfer leading to resurfacing and excessive brush wear. Streaking of the commutator surface denotes the beginning of serious metal transfer to the carbon brush. Copper drag is an abnormal ammount of excessive commutator material at the trailing edge of the commutator bar—although rare, flash over may occur if not corrected. Grooving is caused by an abrasive material in the brush or atmosphere.

Each of the commutator surface problems has a respective signal pattern which may be output by the SM 110. Accordingly, the processor 80 can determine what type of commutator problems exist based on the signal pattern output by the SM 110. Once the processor 80 determines the wear and/or damage condition of the commutator surface it can make troubleshooting recommendations as to the cause of the wear and/or damage condition. For example, the processor 80 can employ a lookup table stored in a memory (not shown) operatively coupled to the processor 80. A representative lookup table is shown in FIG. 8, which provides for narrowing down the possible causes for the wear/damage to the commutator surface. For instance, if the processor 80 determines from the filter output that grooving of the commutator surface has occurred, the processor 80 can inform the user that the likely cause of the condition is either contamination from abrasive dust or caused by an abrasive brush.

It should be appreciated that a single optical fiber 22 may be operatively coupled to both the signal monitor 110 and the interferometric system 40 in order to optimize optical fiber utilization.

Figure 6B:
FIGS. 6b–6e are illustrations of waveforms representative of various surface conditions of a commutator in accordance with the present invention.
Figure 6C:
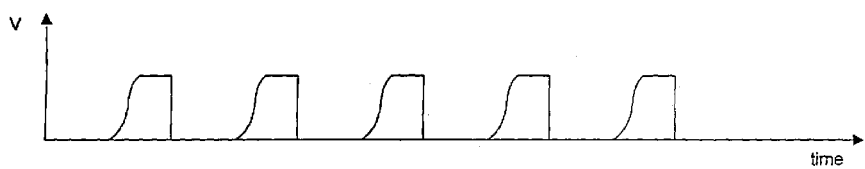
Figure 6D:
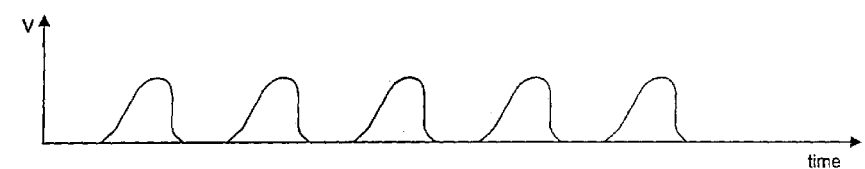

FIGS. 6b–6d are illustrations representative of analog waveforms of the converted reflected measuring beam 56 with respect to various commutator surface conditions. FIG. 6b depicts an analog waveform of a reflected measuring beam $56_s$ for a commutator $30_s$ having a normal surface. In this embodiment, the commutator surface is comprised of many equidistantly spaced bars. As the measuring beam $56_s$ strikes a bar the reflected back measuring beam $56_s$ exhibits a higher amplitude than that reflected off a slot (i.e., space) between adjacent bars. Thus, the analog waveform of a measuring beam $56_s$ reflected off a normal commutator surface will look similar to a square wave wherein the portions of high amplitude represent the measuring beam $56_b$ being reflected off a conductive commutator bar and the portions of low amplitude represent the measuring beam $56_b$ being reflected off a space between two bars.

FIG. 6c illustrates a representative analog waveform of a reflected measuring beam $56_c$ of a commutator surface having leading edge wear of bars of the commutator $30_c$. Leading edge wear of the bars results in the reflected measuring beam $56_c$ having a correspondingly tapered sloped amplitude of the leading edge of the waveform. More particularly, since the amplitude of the reflected measuring beam $56_c$ is a function of the reflectance of the bar, the more abrasively worn portions of the bar will result in a reflected measuring beam $56_c$ having lower amplitude. Thus, as the reflected measuring beam $56_c$ moves initially from the space between two bars(where it has lowest amplitude) then along the worn leading edge of a bar toward the unworn or uniformly worn portion of the bar, the amplitude of the reflected measuring beam $56_c$ increases.

FIG. 6d illustrates a representative analog waveform of a reflected measuring beam $56_d$ of a commutator surface having surface contamination. The surface contamination results in the reflected measuring beam $56_d$ having sloped amplitude as well as lower amplitude as compared to the reflected measuring beam $56_b$ of FIG. 6b.

Figure 6E:

FIG. 6e illustrates a representative analog waveform of a reflected measuring beam $56_e$ of a commutator surface having scratches in the commutator surface. The scratches result in the reflected measuring beam $56_e$ having an irregular and lower amplitude as compared to the reflected measuring beam $56_b$ of FIG. 6b.

It should be appreciated that the analog waveforms illustrated in FIGS. 6b–6d are representative of only a few of many possible analog waveforms of the measuring beam 56 with respect to a variety of commutator surface conditions. Accordingly, the scope of present invention is intended to include the determination of surface conditions of an object that the article 22 is in contact with. The surface condition of the object may be determined by comparing the analog waveform of the measuring beam 56 reflected off the surface of the object and assessing the condition of the surface based on the reflected measuring beam 56. The assessment may be made by comparing the analog waveform against an expected waveform and/or by comparing the analog waveform against a table of waveforms stored in a memory, each of the stored waveforms being indicative of a particular surface condition. Any system, device, means or methodology for analyzing the reflected measuring beam 56 suitable for determining surface conditions may be employed to carry out the present invention and falls within the scope of the claims.

Figure 7:
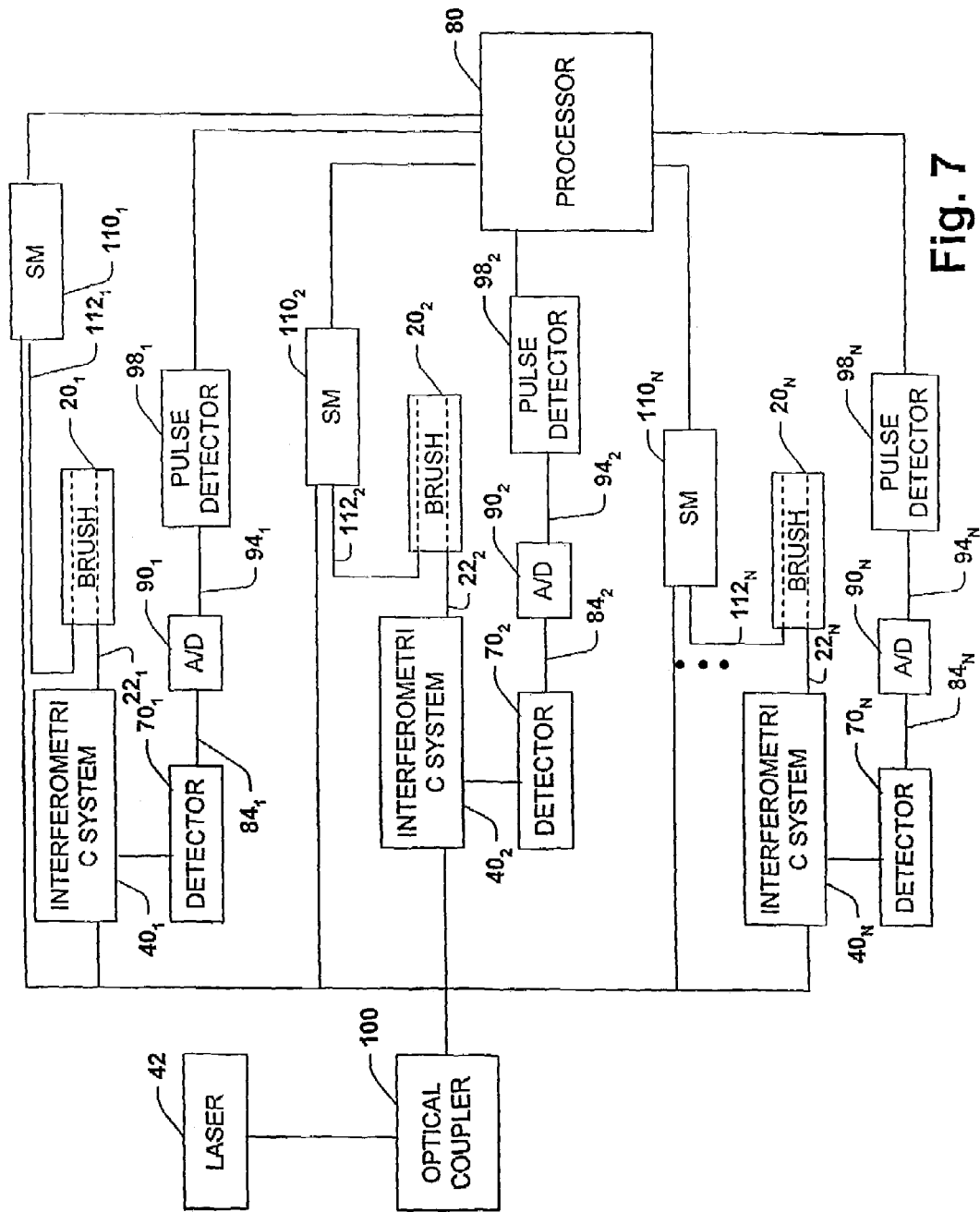
FIG. 7 is a schematic block diagram of another specific aspect of the present invention which provides for the determination of the amount of wear, the rate of wear, and surface assessment in connection with multiple articles in accordance with the present invention.

FIG. 7 is a schematic block diagram of another specific aspect of the present invention. This embodiment is similar to that of FIG. 6a but provides for the determination of the amount of wear, the rate of wear, and surface assessment in connection with multiple articles 20. As mentioned above, in motor applications more than one brush may be employed to provide current to the motor. The number of brushes used corresponds to the number of poles of the motor. In this embodiment, a plurality of interferometric systems 40 and analog signal monitors 110 similar to that of FIG. 6a are employed. According to this aspect of the present invention, the amount of wear, the rate of wear and commutator surface assessment in connection with N number of brushes 20 can be determined. Like reference numerals indicate like parts with respect to FIG. 6a and thus further description of these components is not presented for sake of brevity. Similar to the embodiment described in FIG. 5, the present embodiment maximizes the utilization of the laser 42. Furthermore, designs which share elements among multiple brushes to be monitored and analyzed may also be deployed here.

In addition, either of the embodiments of FIG. 6a or 7 may be employed to determine the speed of a motor. Time-based frequency measurements of the reflected light beam pulses off the commutator surface may be employed to provide indication of motor speed. Precise timing of the reflected pulse train can also be used to provide accurate values for acceleration within the period of 1 shaft revolution.

Figure 9:
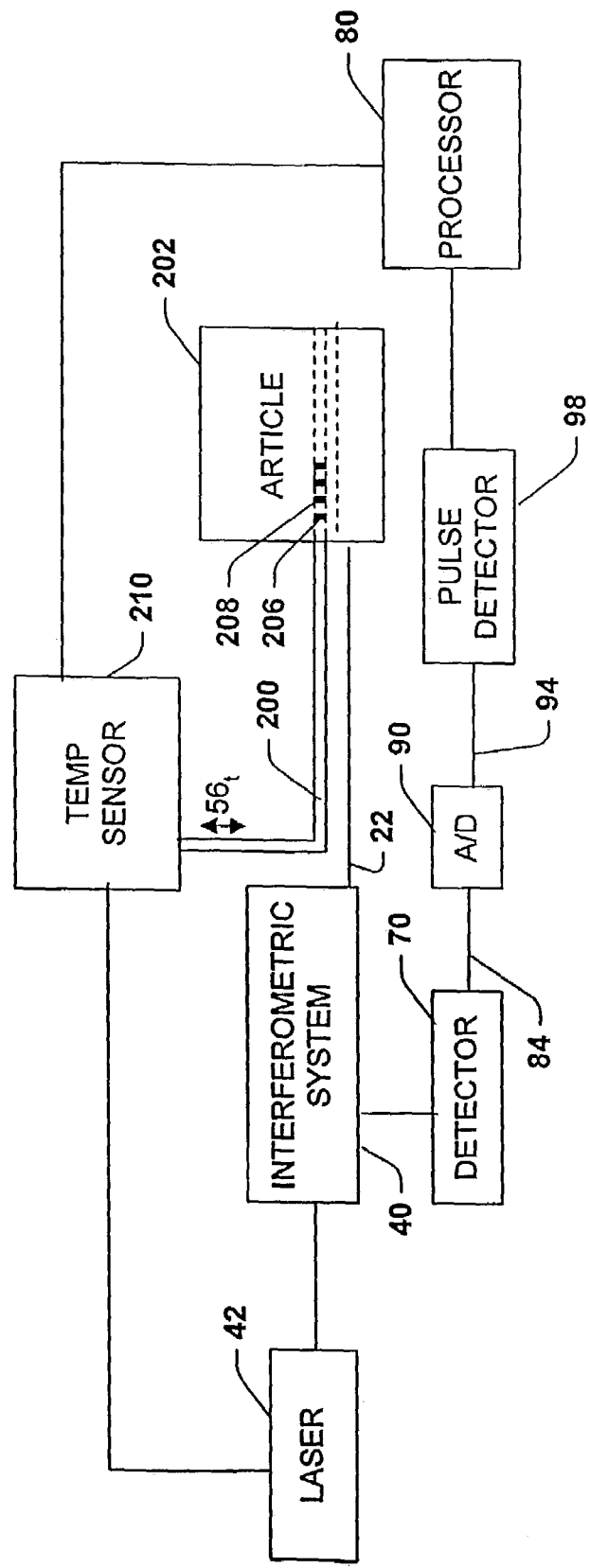
FIG. 9 is a schematic block diagram of another aspect of the present invention which employs a grated optical fiber to facilitate monitoring for changes in temperature in accordance with the present invention.

FIG. 9 is a schematic block diagram of another aspect of the present invention. In this embodiment, an optical fiber 200 with a doping material applied which may be employed to monitor for changes in temperature. This embodiment is similar to the embodiment depicted in FIGS. 4a and 6a, except that the optical fiber 200 is coated so as to have a temperature-sensitive index of refraction in conjunction with a coated surface area to provide for monitoring changes in temperature of article 202 and a temperature sensor 210 is operatively coupled to the optical fiber 200 so as to monitor the reflected measuring beam $56_t$ (similar to the manner discussed above with respect to the embodiment of FIG. 6a) for changes in temperature. Like parts between the embodiments of FIGS. 4a, 6a and 9 include like reference numerals. Further discussion as to parts already discussed is limited for sake of brevity.

The temperature sensor 210 is operatively coupled the optical fiber 200, laser 42 and the processor 80. The temperature sensor 210 provides for directing a measuring beam $56_t$ from the laser 42 to the optical fiber 200. The measuring beam $56_t$ travels through the optical fiber 200, at least a portion of which is embedded in an article such as brush 202. The measuring beam $56_t$ will strike an object that the article 202 is in contact with and be reflected back through the optical fiber 200. The temperature sensor 210 receives the reflected measuring beam $56_t$. The temperature sensor 210 converts the reflected measuring beam $56_t$ to an electrical signal and outputs it to the processor 80. The processor 80 analyzes the signal output by the temperature sensor 210 and is able to make a determination of temperature relating to the article 202.

Deformation or strain on the brush (and on the embedded fiber 200) may occur due to thermal expansion or other pressure related causes. It is to be appreciated that any grating suitable for carrying out the present invention may be employed such as a Fiber Bragg Grating. The optical fiber 200 will be grated such that a change in the index of refraction due to a temperature change will cause a shift in the peak transmission/reflection wavelength of the light being reflected off the grating surface. Temperature estimates of the article surrounding the wave-guide may be made by analyzing the attenuation of the reflected light signal at specific wavelengths. The present invention affords for a temperature sensing system/method that is light in weight, nonobtrusive, substantially insensitive to electromagnetic interference and capable of withstanding extreme conditions including wide temperature extremes, shocks and vibration.

To accomplish such a system/method, fiber gratings are constructed by doping the core of the optical fiber 200 with material such as germania. When exposed to light, the index of refraction of an optical core of silica based fiber with appropriate core dopants has been observed to have a modified index of refraction. By using phase masks or interfering laser beams as discussed above, it is possible to produce multiple variations in the index of refraction along the length of the fiber core producing an internal grating structure. Adjusting the spacing of the period during formation of the fiber grating changes its spectral transmission and reflection characteristics. When the optical fiber 200 is subject to longitudinal strain or compression along its length axis, the fiber gratings 206, 208 expand or contract causing a spectral shift that may be measured to determine longitudinal strain. By having two separated wavelengths for the fiber gratings 206, 208, respectively, $\lambda_1$ and $\lambda_2$, temperature changes as well as longitudinal changes of the optical fiber 200 may be measured. It should be appreciated that for measuring temperature of the article 202, an end of the optical fiber 20 may terminate within the article 202 rather than at a surface of the article 202.

Thus, by embedding the optical fiber 200 in an article such as a carbon brush 202, the amount of wear, the rate of wear and temperature fluctuations of the carbon brush 202 can be monitored. More specifically, the interferometric techniques discussed above with respect to measuring the amount of wear and the rate of wear of the carbon brush 20 may be combined with the grating system of FIG. 9 to result in a system which provides for monitoring several parameters relating to wear and temperature.

It will be appreciated that any suitable technique for grating the fiber optic cable 200 may be employed to carry out the present invention. U.S. Pat. No. 5,591,965 entitled Multiparameter Sensor System Using Multiple Grating Fiber Optic Birefringement Fiber teaches an exemplaray system of fiber optic grating, and this patent is incorporated herein by reference in its entirety.

Figure 10:
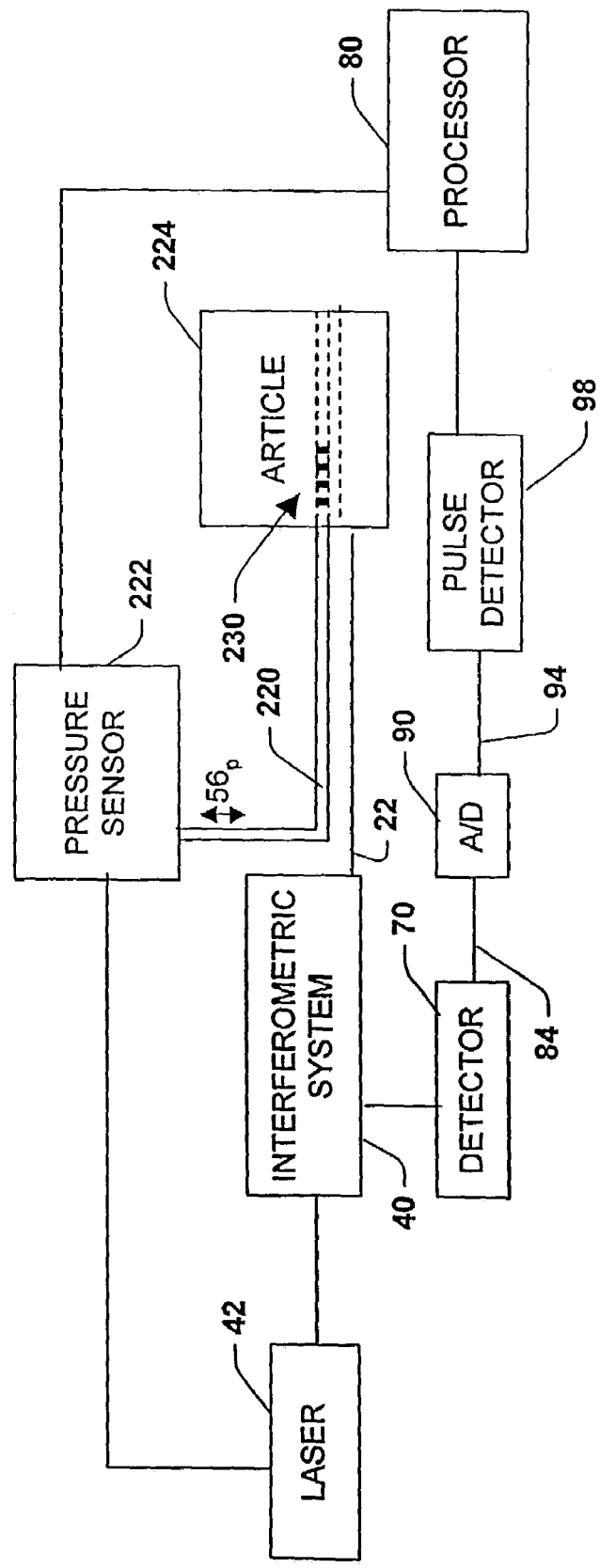
FIG. 10 is a schematic block diagram of another aspect of the present invention in which an optical fiber is employed to facilitate monitoring for changes in pressure in accordance with the present invention.

Turning now to FIG. 10, a schematic block diagram of another aspect of the present invention is shown. In this embodiment, an optical fiber 220 is employed which may be employed to monitor for changes in pressure. This embodiment is similar to the embodiment depicted in FIGS. 4a, 6a and 9 except that the optical fiber 220 includes microbends 230 to provide for monitoring changes in pressure relating to an article/environment 224. Like parts between the embodiments of FIGS. 4a, 6a and 9 include like reference numerals. Further discussion as to parts already discussed is limited for sake of brevity.

A pressure sensor 222 is operatively coupled to the optical fiber 220, laser 42 and the processor 80. The pressure sensor 222 provides for directing a measuring beam $56_p$ from the laser 42 to the optical fiber 220. The measuring beam $56_p$ travels through the optical fiber, at least a portion of which is embedded in an article such as brush 224. The measuring beam $56_p$ will strike an object that the article 224 is in contact with and be reflected back through the optical fiber 220. The pressure sensor 222 receives the reflected measuring beam $56_p$. The pressure sensor 222 converts the reflected measuring beam $56_p$ to an electrical signal and filters the signal such that a predetermined bandwidth is output to the processor 80. The processor 80 analyzes the signal output by the pressure sensor 222 and is able to make a determination of pressure relating to the article 224.

More particularly, the optical fiber 220 will undergo micro-bending as a result of pressure applied thereto. The affect of this bending is an attentuation of the measuring light beam $56_p$, which varies in relation to the amount of bending of the optical fiber 220. Accordingly, the optical fiber 220 can be employed to provide pressure data relating to the article/medium 224 it is exposed to. For instance, if the optical fiber 220 is embedded in an article such as a carbon brush, the optical fiber 220 can provide data relating to the pressure the carbon brush is exposed to. Similarly, if the optical fiber 220 is placed in an environment such as a pump chamber, the optical fiber can provide data relating to the pressure within the pump chamber. Additionally, by exposing the optical fiber 220 to the interior of a tire, pressure information relating to the inflation of the tire may be obtained.

A section of the optical fiber 220 contains a plurality of permanently induced microbends 230, that is, random or periodic undulations in the longitudinal axis of the optical fiber 220, which are typically small in amplitude relative to the diameter of the optical fiber 220. In a preferred embodiment, the microbends 230 are periodic and quasi-sinusoidal. As the pressure surrounding the fiber cable 220 changes, the optical output correspondingly changes because the pressure change affects the amplitude of the induced microbends 230 which in turn affects the optical transmissivity of the optical fiber 220. The increase or decrease in the output of the optical fiber 220 may be employed to monitor pressure changes the optical fiber 220 is exposed to. Any suitable technique for inducing microbends may be employed to carry out the present invention. It should be appreciated that for measuring pressure of the article 224, an end of the optical fiber 220 may terminate within the article 224 rather than at a surface of the article 224.

By combining various embodiments discussed above with respect to measuring the amount of wear and the rate of wear of the carbon brush 20 with the pressure sensing embodiment of FIG. 10 a system results which provides for monitoring several parameters relating to wear and pressure of an article the fiber optic cable 220 is embedded in.

It is to be appreciated that the grating technique discussed above with respect to FIG. 9 and the microbending technique of FIG. 10 may be combined together with other aforementioned embodiments of the present invention to provide a multi-parameter sensing system which provides for the monitoring of article wear, rate of wear, article temperature and article pressure.

Figure 11:
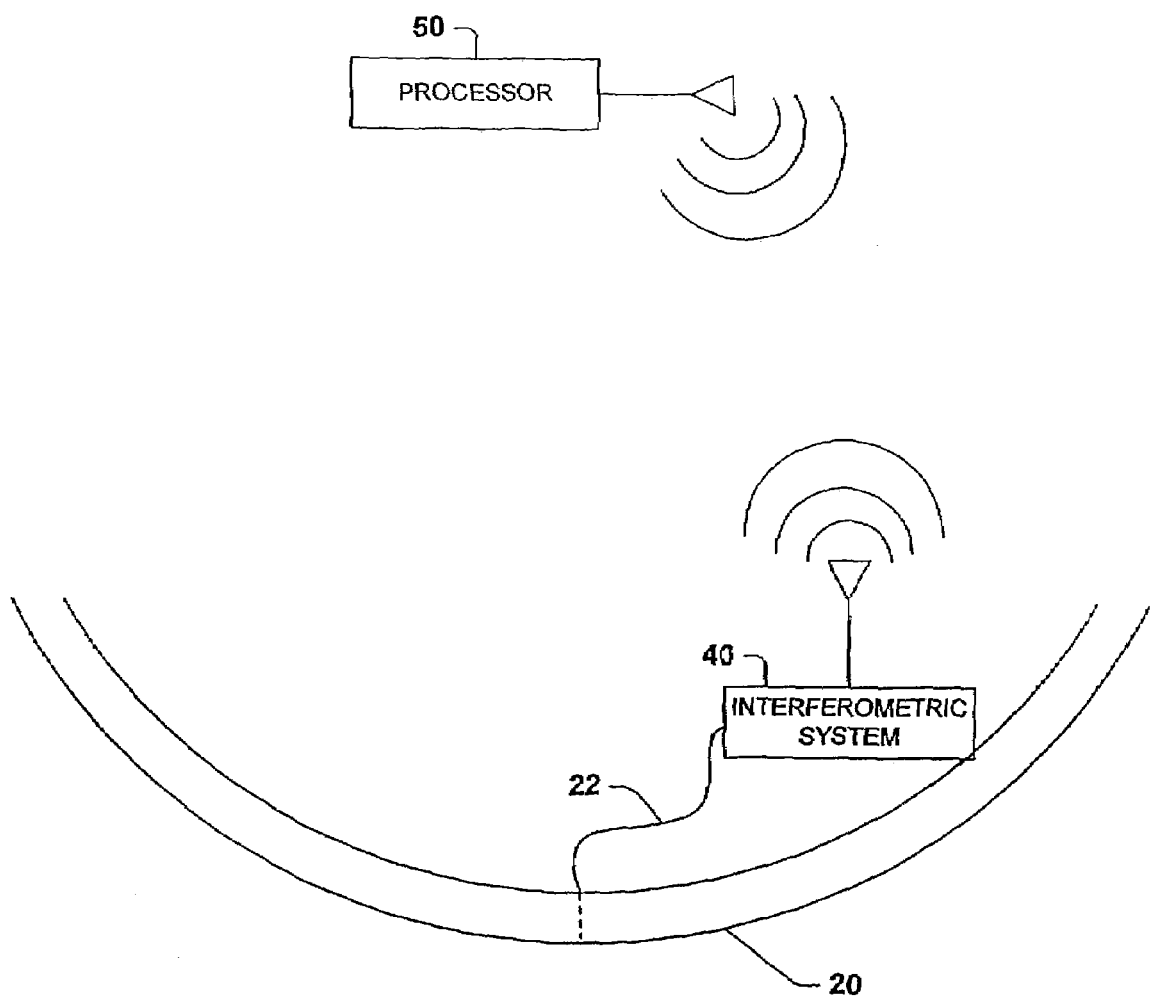
FIG. 11 is a schematic diagram illustrating the present invention as employed in a tire.

FIG. 11 is a schematic diagram illustrating the present invention as employed in a tire 20. As mentioned above, the present invention may be employed to analyze wear, rate of wear, and/or temperature and/or pressure information relating to the tire 20. Information obtained by the interferometric system may be transmitted wirelessly to the processor 50. It will be appreciated that a temperature sensor or pressure sensor may be employed in place of or in addition to the interferometric system 40. In the case of wireless operation, power may be scavaged from the environment or generated locally to power the system using known techniques(e.g., inductive power generation).

Figure 12:
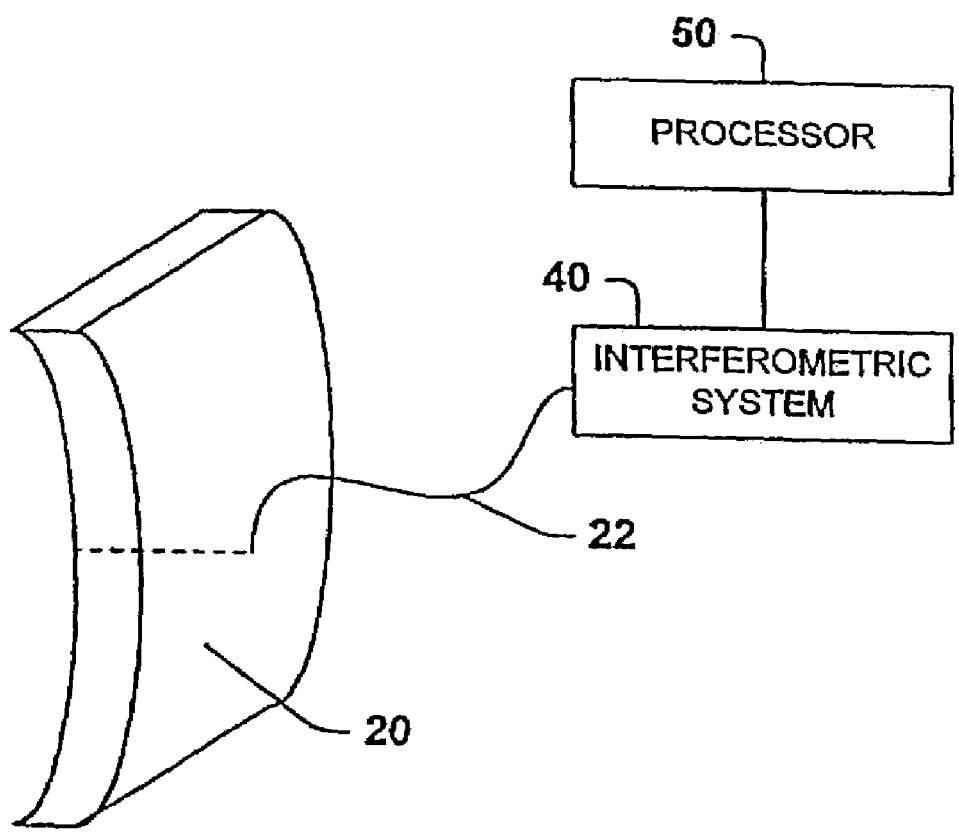
FIG. 12 is a schematic diagram illustrating the present invention as employed in a brake pad.

FIG. 12 is a schematic diagram illustrating the present invention as employed in a brake pad 20. As mentioned above, the present invention may be employed to analyze wear, rate of wear, and/or temperature and/or pressure and surface information relating to the brake pad 20. It will be appreciated that a temperature sensor or pressure sensor may be employed in place of or in addition to the interferometric system 40.

Figure 13:
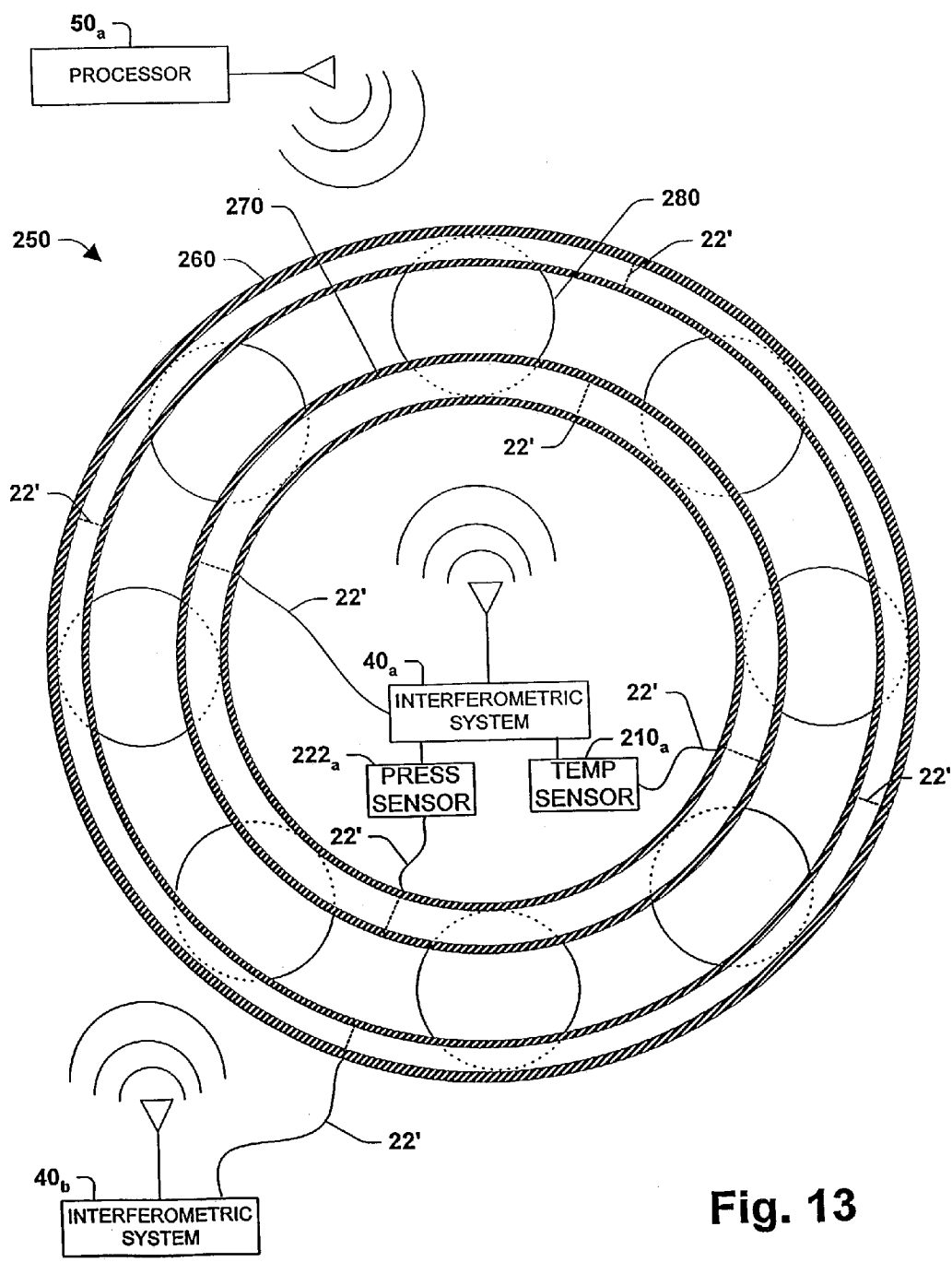
FIG. 13 is a schematic diagram illustrating the present invention as employed in a bearing.

It is further to be appreciated that the present invention can be employed to analyze wear, rate of wear, and/or temperature and/or pressure information as it relates to motors. Typically, a shaft (not shown) is coupled to the rest of a motor by a pair of bearings. FIG. 13 illustrates a ball bearing 250 making up one of a pair of ball bearings employed in a motor. It will be appreciated that other sorts of bearings (e.g., roller bearings, sleeve bearings, hydrodynamic bearings, etc.) may alternatively be used to couple the shaft to the rest of the motor. It will further be appreciated that more than two bearings may be employed to rotatably couple the shaft to the rest of the motor. Although, the present invention is described with respect to ball bearings other bearings such as sleeve bearings, hydrodynamic bearings, double row ball bearings and thrust bearings may be measured according to the present invention. For example, in the case of hydrodynamic bearings, the wear sensor can be used to determine the wear and rate of wear of the babbitt. The processor may then determine(forecast)when the bearing needs to be re-babbitted. Additionally, the sensor can be employed to determine the state of any lubrication, for example, the lack of lubrication or the color of the lubrication (e.g., opaque) to provide health status of the bearing or lubrication.

The bearing 250 has an outer race 260, an inner race 270, and a set of balls 280 therebetween. A number of optical fibers 22' are shown embedded in the outer race 260 and the inner race 270, such that one end of the fibers 22' are exposed to the balls 280. The other end of the optical fiber 22' is shown operatively coupled to an interferometric system $40_a$ for the inner race 270 and $40_b$ for the outer race 260. The interferometric system $40_a$ and $40_b$ are operatively coupled to a processor $50_a$. It is to be appreciated that the interferometric system $40_a$ and $40_b$ can be integrated and even attached to the end of the inner race 270 and the outer race 260, respectively, away from the set of balls 280. Furthermore, the interferometric systems $40_a$ and $40_b$ may include a wireless transceiver for wirelessly transmitting data to the processor $50_a$. Power may be scavaged from the environment or generated locally using known techniques such as inductive power generation.

It is to be appreciated that interferometric system $40_a$ and $40_b$ may be coupled to processor $50_a$ using direct wire links or even network links. Processor $50_a$ may also be integrated with the interferometric systems and located at the article (e.g., bearing) or located remotely using only a fiber link to the article to provide a smart bearing. A similar scheme may exist for sharing system elements when multiple sensors are deployed. Although, a single interferometric system is shown coupled directly to a single optical fiber 22' for both the outer race 260 and the inner race 270, each optical fiber 22' in the outer race 260 can be coupled to the interferometric system $40_b$ and each optical fiber in the inner race 270 can be coupled to the interferometric system $40_a$. Furthermore, each optical fiber 22' can include a dedicated respective interferometric system.

At least one of the optical fibers 22' could include a grating employed to sense changes in temperature, similar to that described in FIG. 9. This optical fiber 22' can be coupled to a temperature sensor $210_a$ for transmitting temperature data to the processor $50_a$ via the interferometric system $40_a$. Additionally, at least one of the optical fibers 22' can include microbends employed for monitoring changes in pressure, similar to that described in FIG. 10. This optical fiber 22' can be coupled to a pressure sensor $222_a$ for transmitting pressure data to the processor $50_a$ via the interferometric system $40_a$. Optical fibers may also be employed to measure radial and axial wear on the bearing raceways. All of these parameters can be combined using sensor fusion to establish device health or state, fault mode, and control actions based on warnings or recommendations.

The present invention can be employed in other technologies, such as semiconductor fabrication. Semiconductor wafers undergo Chemical Mechanical Polishing (CMP) steps several times in modern fabrication. CMP is used to thin a wafer as well as planarizing the dielectric between metal layers. An accurate method of determining the amount of material removed is crucial for the successful fabrication of these wafers. One or more optical waveguides or fibers can be embedded in the semiconductor wafer. The waveguides will be embedded in at least the center and near the periphery of the wafer. Multiple points of observation allow additional data to be gathered on the wafer to monitor wafer distortion and planarization and non-uniformity of process. The waveguides can be formed by doping variations in the semiconductor, embedding an optical fiber in a hole drilled by optical, mechanical or chemical means, or filling in a hole with a material that has an index of refraction greater than the silicon, passivation layers and polishing compound. Coherent light can then shine through the light waveguides and be reflected back from the interface between the wafer and the polishing material. The length of the light waveguide is determined by the interference pattern created by the reflected light and a reference path.

For example, FIGS. 14a–14f illustrate the use of an optical fiber in forming and polishing contacts in a semiconductor wafer. With regard to the description in connection with the example of FIGS. 14a–14f, the term substrate includes not only a semiconductor substrate, but also any and all layers and structures fabricated over the semiconductor substrate up to the point of processing under discussion.

Figure 14A:
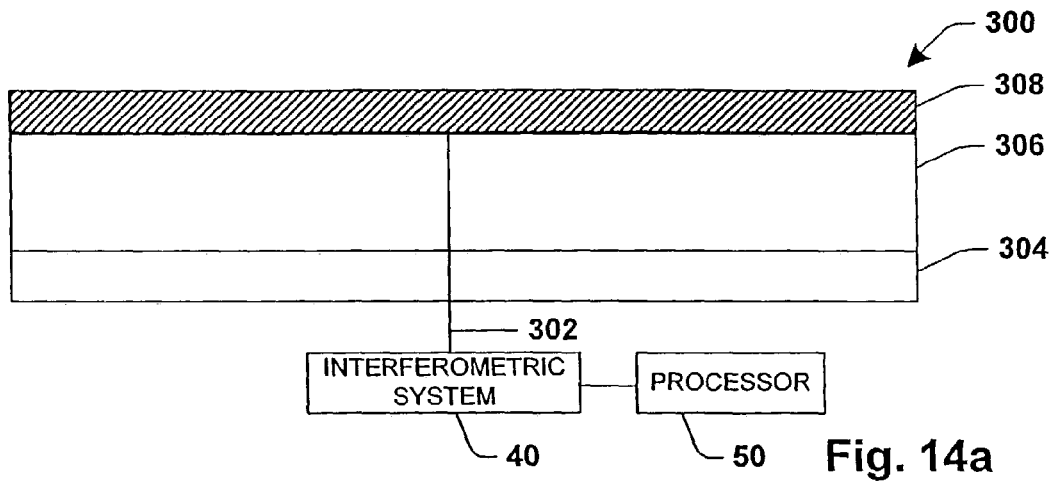
FIGS. 14a–14f illustrate the use of an optical fiber in forming and polishing contacts in a semiconductor wafer in accordance with the present invention.

FIG. 14a illustrates a semiconductor device 300 including an insulating layer 306 which is formed on a semiconductor substrate 304. Semiconductor substrate 304 may be any suitable semiconductor material, for example, a monocrystalline silicon substrate. Any suitable technique (e.g., thermal oxidation, plasma enhanced chemical vapor deposition (CVD), thermal enhanced CVD and spin on techniques) may be employed in forming the insulating layer 304. Preferably, the insulating layer 306 is silicon dioxide ($SiO_2$) with a thickness of about 0.8 to 1.0 microns. Other usuable insulating materials are silicon nitride ($Si_3N_4$), (SiN), silicon oxynitride ($SiO_xN_y$), and flourinated silicon oxide ($SiO_xF_y$), and polyimide(s). An optical fiber 302 is embedded in the semiconductor device 300 running perpendicular to the top surface of the semiconductor device 300. The optical fiber is coupled to an interferometric system 40 and a processor 50 as previously described. The optical fiber 302 should be made of a material conducive to semiconductor processing. The optical fiber 302 is positioned in a location which is in contact with the surface to be formed. However, a number of optical fibers may be embedded in a semiconductor substrate that is used in forming a number of contacts and vias and/or controlling uniformity in a layer polishing or removal on a semiconductor substrate.

A thin photoresist layer 308 is formed on the insulating layer 306. The thin photoresist layer 308 has a thickness of about 500D–5000D, however, it is to be appreciated that the thickness thereof may be of any dimension suitable for carrying out the present invention. Accordingly, the thickness of the thin photoresist layer 308 can vary in correspondence with the wavelength of radiation used to pattern the thin photoresist layer 308. One aspect of the present invention provides for forming the thin photoresist layer 308 to have a thickness within the range of 1000D to 4000D. Another aspect of the present invention provides for forming the thin photoresist layer 308 to have a thickness within the range of 2000D to 3000D. Yet another aspect of the present invention provides for forming the thin photoresist layer 308 to have a thickness within the range of 500D to 2000D. The thin photoresist layer 308 may be formed over the insulating layer 306 via conventional spin-coating or spin casting deposition techniques.

Figure 14B:
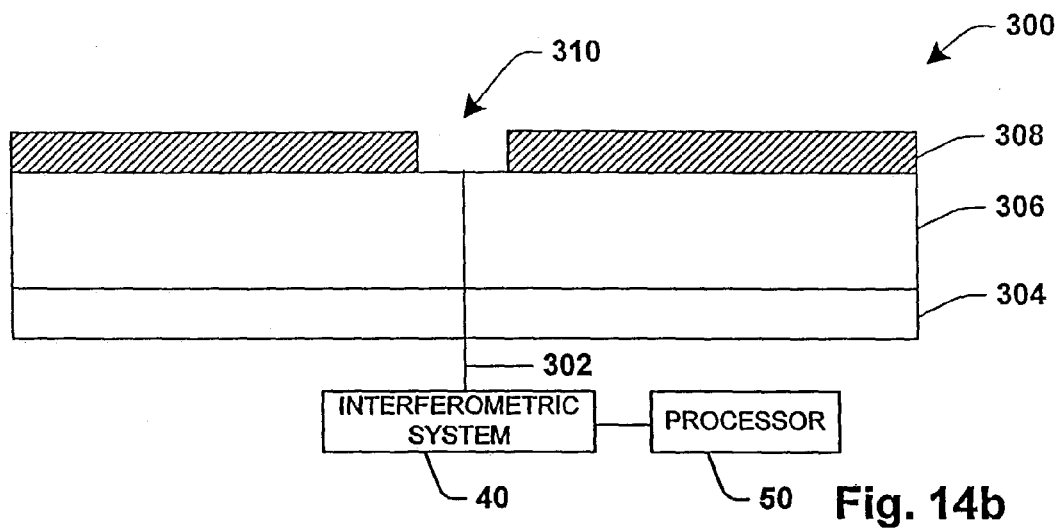
Figure 14C:
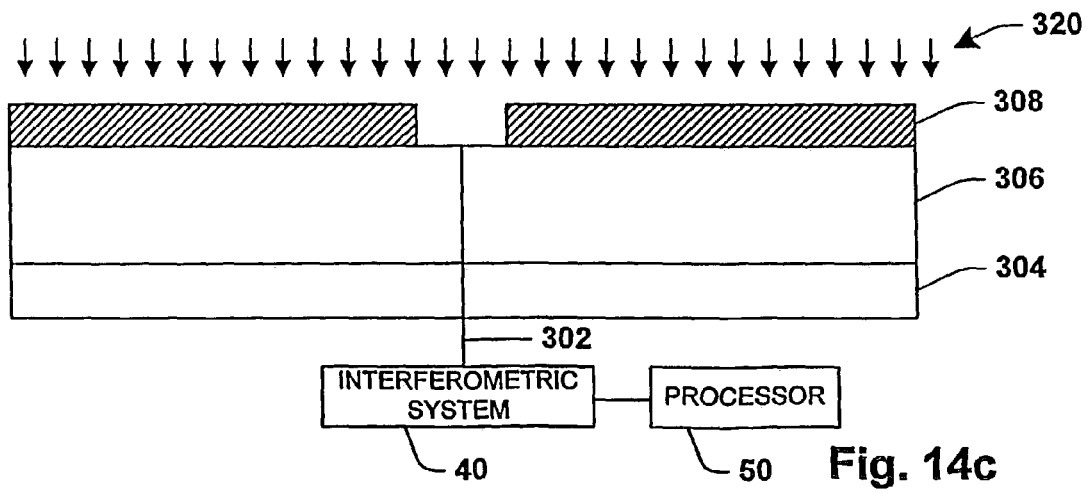

The thin photoresist layer 308 has a thickness suitable for functioning as a mask for etching the underlying insulating layer 306 and for forming patterns or openings in the developed thin photoresist layer 308. The photoresist layer 308 is patterned using conventional techniques to form a first opening 310 (FIG. 14b). The size of the first opening 310 is about the size of the ultimate via. The patterned photoresist 308 serves as an etch mask layer for processing or etching the underlying insulating layer 306.

An etch step 320 (e.g., anisotropic reactive ion etching (RIE)) (FIG. 14c) is performed to form a via 315 (FIG. 14d) in the insulating layer 306. The patterned photoresist 308 is used as a mask for selectively etching the insulating layer 306 to provide a patterned insulating layer 306. Any suitable etch technique may be used to etch the insulating layer 306. Preferably, a selective etch technique may be used to etch the material of the insulating layer 306 at a relatively greater rate as compared to the rate that the material of the patterned photoresist 308 is etched. The optical fiber 302 can be used to measure and control the depth of the etching step 320 such as through surface light loss. The optical fiber 302 can also provide depth information to the processor 50 via the interferometric system 40. This information can be transmitted to the anisotropic reactive ion etcher to control the extent of the etching. Alternatively, a second optical fiber 302' can be employed for limiting the etching depth. The second optical fiber 302' can have a length such that a measuring end of the second optical fiber 302' extends to the desired depth of the via 315.

Figure 14D:
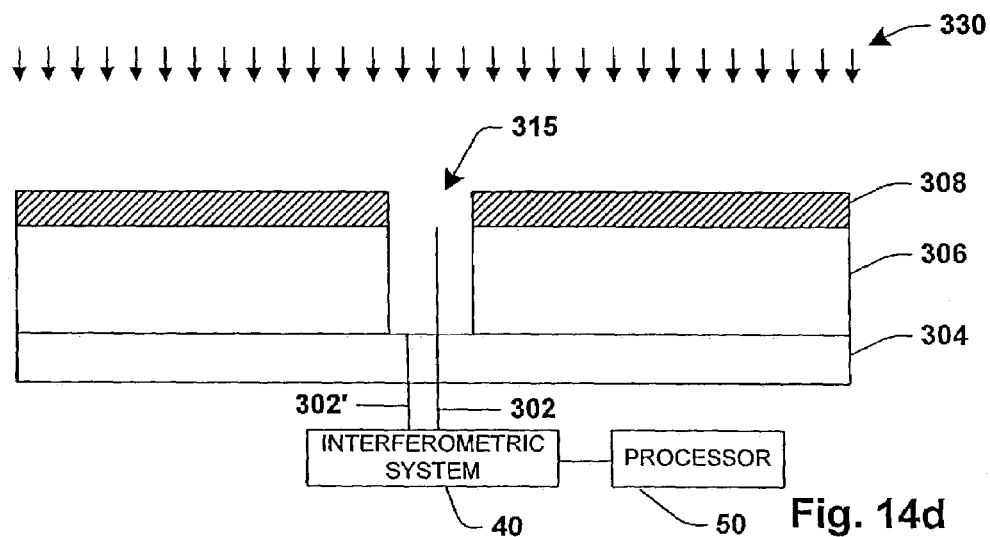
Figure 14E:
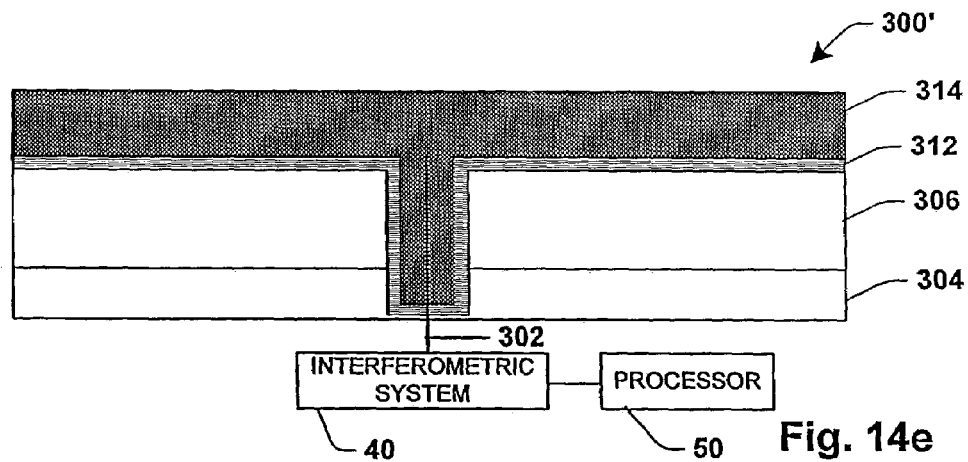
Figure 14F:
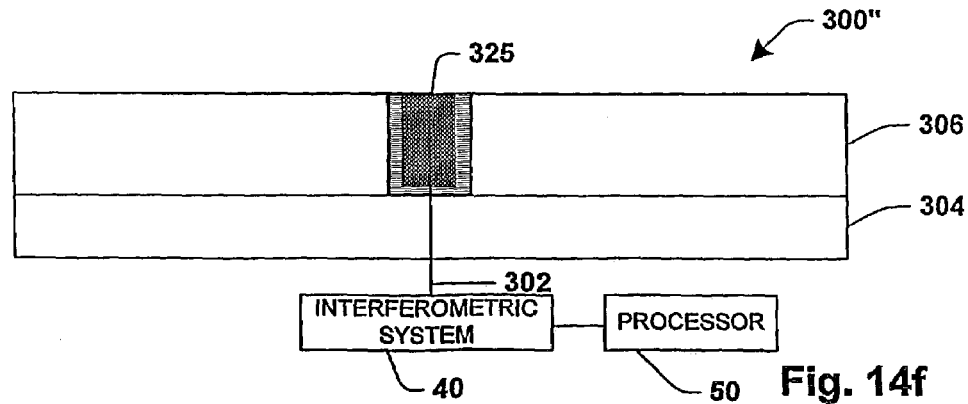

FIG. 14*d* illustrates a stripping step 330 (e.g., ashing in an $O_2$ plasma) to remove remaining portions of the photoresist layer 308. Next, a deposition step is performed on the structure 300' (FIG. 14*e*) to form a protective layer 312 over the structure 300'. The deposition step also includes depositing a metal contact layer 314. FIG. 14*f* illustrates the structure 300" after a polished back step has been performed to remove a predetermined thickness of the protective layer 312 and the metal contact layer 314. The polish back step includes using a polish that is selective to removing the metal layer as compared to the insulating layer.

As can be seen in FIGS. 14*a*–14*f,* the optical fiber 302 is embedded in the semiconductive structure 300. The optical fiber 302 is embedded such that its length direction is substantially parallel to the direction of polishing of the semiconductive structure. Thus, as the semiconductive structure 300 is polished, the end of the optical fiber 302 will similarly wear and the length of the optical fiber 302 decreases. Since the optical fiber 302 is made of a material conducive to semiconductor processing, the optical fiber 302 wears substantially at the same amount and rate as the semiconductive structure which the optical fiber 302 is embedded in. Again the interferometric system 40 can provide this information to the processor 50 for controlling the amount and uniformity of the polishing step. Substantial completion of the polished back step results in a structure 300" shown in FIG. 14*f.* The structure 300" includes the semiconductor substrate 304, the insulating layer 306 and a contact 325 connecting the semiconductor substrate 304 to a top surface of the insulating layer 306.

The polishing and buffing pads used in the CMP process in addition to polishing and buffing pads used for other processes also exhibit wear and can employ optical fibers to measure this wear. Polishing and buffing pads become thinner due to mechanical loss of material as they polish and buff. These pads need to be replaced when they become too thin. Monitoring their thickness during polishing/buffing allows a timely and resource efficient method of determining when to replaced the pad.

Figure 15:
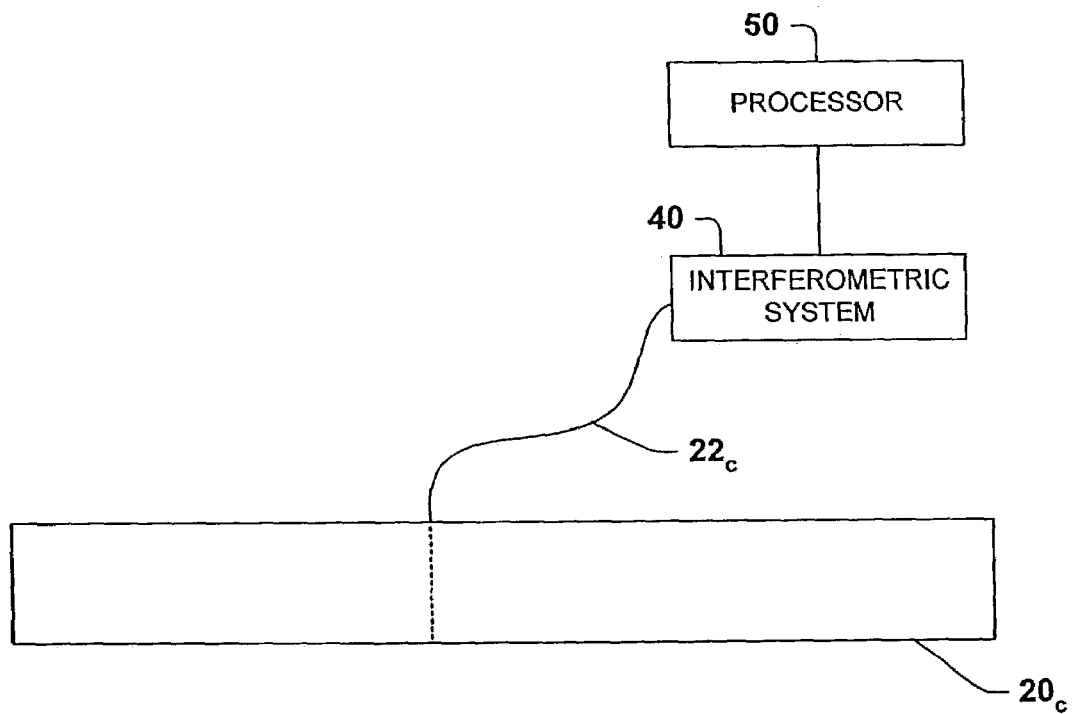
FIG. 15 is a schematic diagram illustrating the present invention as employed in a polishing pad.

Fiber optics can be embedded through a pad as illustrated in FIG. 15. A pad 20$_c$ includes an optical fiber 22$_c$ embedded therein. The optical fiber 22$_c$ is coupled to an interferometric system 40 linked to a processor 50. As the pad 20$_c$ becomes thinner, the length of the fiber will change. Injecting a coherent light source into the fiber and observing the interference patterns developed by the reflected light allows accurate measurement of material wear. Preferably, the fiber optic material (and its cladding) is of the same hardness (or less) as the buffing pad 20$_c$ and the material should not degrade the polishing operation.

Figure 16A:
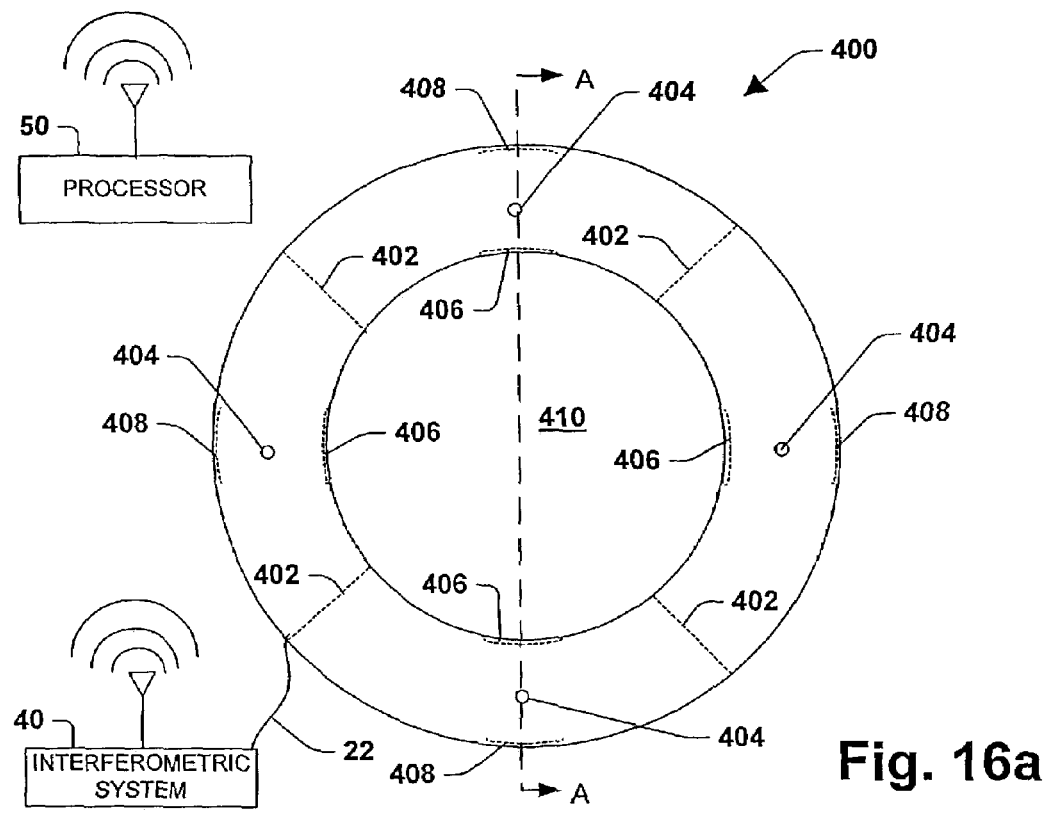
FIG. 16a is a partial schematic diagram illustrating the present invention as employed in a seal.
Figure 16B:
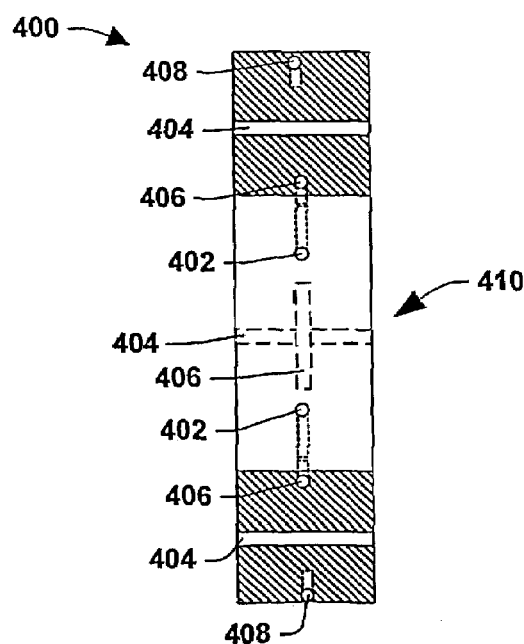
FIG. 16b is cross-sectional view of the seal of FIG. 16a along the lines A—A.

In another aspect of the invention, an optical fiber is embedded in a seal, such as that used in a pump, and a light source is introduced into the fiber. FIGS. 16*a*–16*b* illustrate a seal 400 including a plurality of optical fibers embedded therein. The seal 400 is an annular seal, such as that found surrounding a shaft of a pump or the like. However, any size or shaped seal could include an optical fiber embedded therein. For example, an optical fiber can be embedded within a lip or undulation portion of a seal. Furthermore, different optical fibers can be oriented differently to measure different areas of wear or for measuring different conditions of the seal. The fiber type, fiber orientation, fixturing, and doping of the optical fiber will determine the parameters which may be measured. For example, a fiber embedded radially into the seal will have one end extending through the outer diameter of the seal and the other end extending to the inner diameter to the wear surface of the seal. Since the fiber tip will wear along with the contact surface of the seal against the rotating shaft, the seal wear can be measured in real time and with a high degree of accuracy using interferometric techniques or the like.

The seal 400 includes a central opening 410 adapted to receive a shaft (not shown). The plurality of optical fibers include radial fibers 402, axial fibers 404, inner circumferential fibers 406 and outer circumferential fibers 408. The optical fibers can be utilized in providing information regarding various conditions with respect to the operation and health of the seal. A bragg grating and selected doping materials may be formed in the embedded optical fiber to measure conditions such as seal temperature, seal compression, thermal expansion and deformation of the seal. Additionally, the optical fibers can be employed in measuring characteristics in lubricating film, such as thickness and variation over time, fluid advancement rate, geometry, contaminants and potential cavitation. A series of parallel optical fibers may also monitor the advancing edge of the fluid film as the seal wears. A group of fibers may also image the rotating metal shaft through the lubricating film to detect signs of shaft wear. The interferometric system may also determine the radial displacement(i.e. run out)of the shaft to a high degree of accuracy. This provides other useful diagnostic information such as worn bearings or bent shafts.

The other end of the optical fiber 402 is shown operatively coupled to an interferometric system 40. The interferometric system 40 is operatively coupled to a processor 50. It is to be appreciated that the interferometric system 40 and the processor 50 can be integrated and even attached to the end of the seal 400. Furthermore, the interferometric systems 40 may include a wireless transceiver for wirelessly transmitting data to the processor 50. In one aspect of the invention, the interferometric system 40 and the processor 50 can be integrated into the seal to provide a smart seal. The smart seal can provide a health diagnostics signal via a wire or a wireless transmission. For wireless operation power may be generated locally from the moving structure using known power generation techniques(e.g., inductive power generation). Although, a single interferometric system is shown coupled directly to a single optical fiber 402, each optical fiber 402, 404, 406 and 408 can be coupled to the interferometric system 40. Furthermore, each of the optical fibers 402, 404, 406 and 408 can include a dedicated respective interferometric system.

At least one of the optical fibers 402, 404, 406 and 408 could include a grating employed to sense changes in temperature, similar to that described in FIG. 9. This optical fiber can be coupled to a temperature sensor for transmitting temperature data to the processor 50 via the interferometric system 40. Additionally, at least one of the optical fibers can include microbends employed for monitoring changes in pressure, similar to that described in FIG. 10. This optical fiber can be coupled to a pressure sensor for transmitting pressure data to the processor 50 via the interferometric system 40. All of these parameters can be combined using sensor fusion to establish device health or state, fault mode, and control actions based on warnings or recommendations.

Information regarding the seal performance such as indicated above provides the necessary state information to enable close loop control over the radial force applied to the seal. This can enable the seal to be effective even at very low speeds and measure operating conditions such as viscosity, temperature, and wear change. A very low cost, limited range actuator such as a piezo-based device may provide the real-time control of seal pressure. The piezo-based device can be embedded throughout the seal or in specific contact areas to control the pressure against the surface that the seal is engaging.

Operating the seal at or near optimal conditions holds the promise of significantly extending the life of seals by minimizing seal wear over a wide range of operating conditions and also allowing the seal to be effective even after substantial wear has occurred. Finally, the safety of systems which require a high degree of seal integrity can be enhanced since notification may be provided before actual seal failure and leakage has occurred. Notification can be provided if seal wear is occurring at an abnormal or accelerated rate due to seal defects or process problems. Additionally, heuristic, stochastic, and analytical models of seals can be employed to establish the remaining useful life of a seal and predict when the seal will fail. This provides the critical information needed for condition-based maintenance (proactive) on one of the most critical and failure-prone components in industrial systems. Since closed-loop compensating/optimizing control may also be employed, the seal system may continue to operate at a suboptimal level with perhaps less efficiency or even accelerated wear, while for example avoiding leakage of caustic or explosive fluids and controlling the time to failure of the seal and avoiding an unscheduled shutdown or catastrophic failure.

Figure 17A:
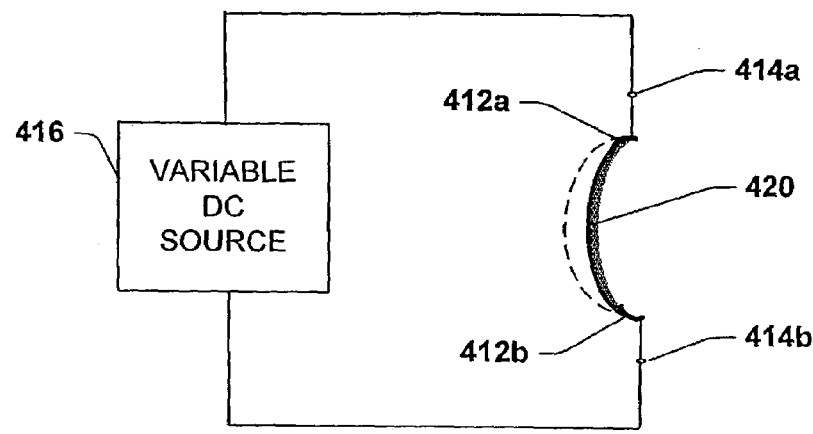
FIG. 17a is schematic diagram of a piezoelectric device coupled to an adjustable power source in accordance with one aspect of the invention.

FIG. 17a illustrates the operation of a piezoelectric device 420 in accordance with the present invention. The piezoelectric device 420 can be embedded in a seal for controlling the flexing of the seal and thus the seal pressure with respect to a contact surface. The piezoelectric device 420 is mounted in the form of a radially defined arc at non-movable fixed locations 412a and 412b. Affixed to the piezoelectric material 420 are electrodes 414a and 414b which are connected to a variable power source 416 (e.g., DC power). When voltage is applied by the variable power source 416 to the piezoelectric device 420, the radially defined arc of the piezoelectric material 420 is caused to expand and/or contract in a radially defined direction as depicted by the dotted line in FIG. 17a. The variable power source 416 allows for voltage applied to the piezoelectric device 420 to be varied resulting in the adjustment of the angle of the piezoelectric device 420. This allows for expansion and/or contraction of the seal and adjustment of the seal pressure against a seal contacting surface.

Figure 17B:
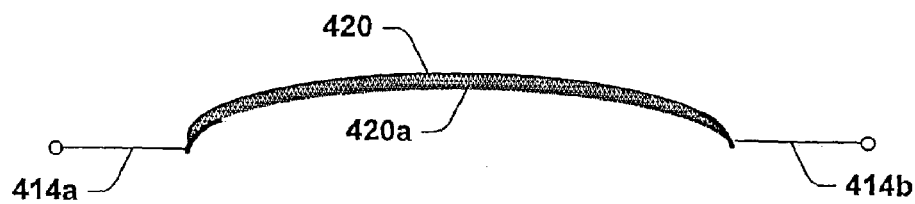
FIG. 17b is a top view of a piezoelectric device in accordance with one aspect of the invention.
Figure 17C:
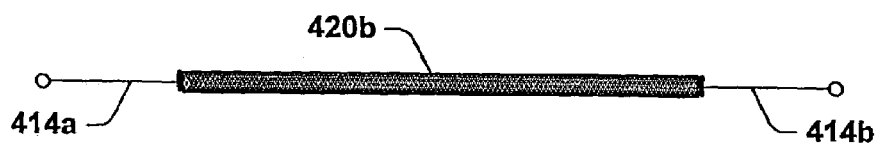
FIG. 17c is a top view of an alternate piezoelectric device in accordance with one aspect of the invention.
Figure 17D:
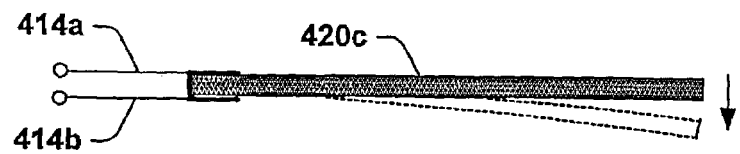
FIG. 17d is a top view of yet another alternate piezoelectric device in accordance with one aspect of the invention.

Now referring to FIG. 17b, a detailed drawing of the radially-arced piezoelectric device 420 is illustrated. As shown, electrodes 414a and 414b are attached to a first and second end of a single layer of piezoelectric device 420. When voltage is applied to the ends of the material as shown in FIG. 17a, the curvature of the formed arc changes because of an elongation in the crystalline structure of the piezoelectric device 420. Turning now to FIG. 17c, another example of a piezoelectric device is illustrated. In this example, the piezoelectric device 420b is formed as a straightened single layer with electrodes 414a and 414b attached at opposing ends as shown in FIG. 17b. As voltage 416 is applied, the piezoelectric device lengthens and contracts in a straight line causing the piezoelectric device to radially deflect inward or outward. A piezoelectric device 420c is shown in FIG. 17d, with electrodes 414a and 414b at the same end of the material. When a voltage is applied to the piezoelectric material 420c, a bend may occur in the direction of the arrow toward the dotted line as shown, for example. Bends may occur in the opposite direction if an opposite polarity voltage is applied.

Figure 18A:
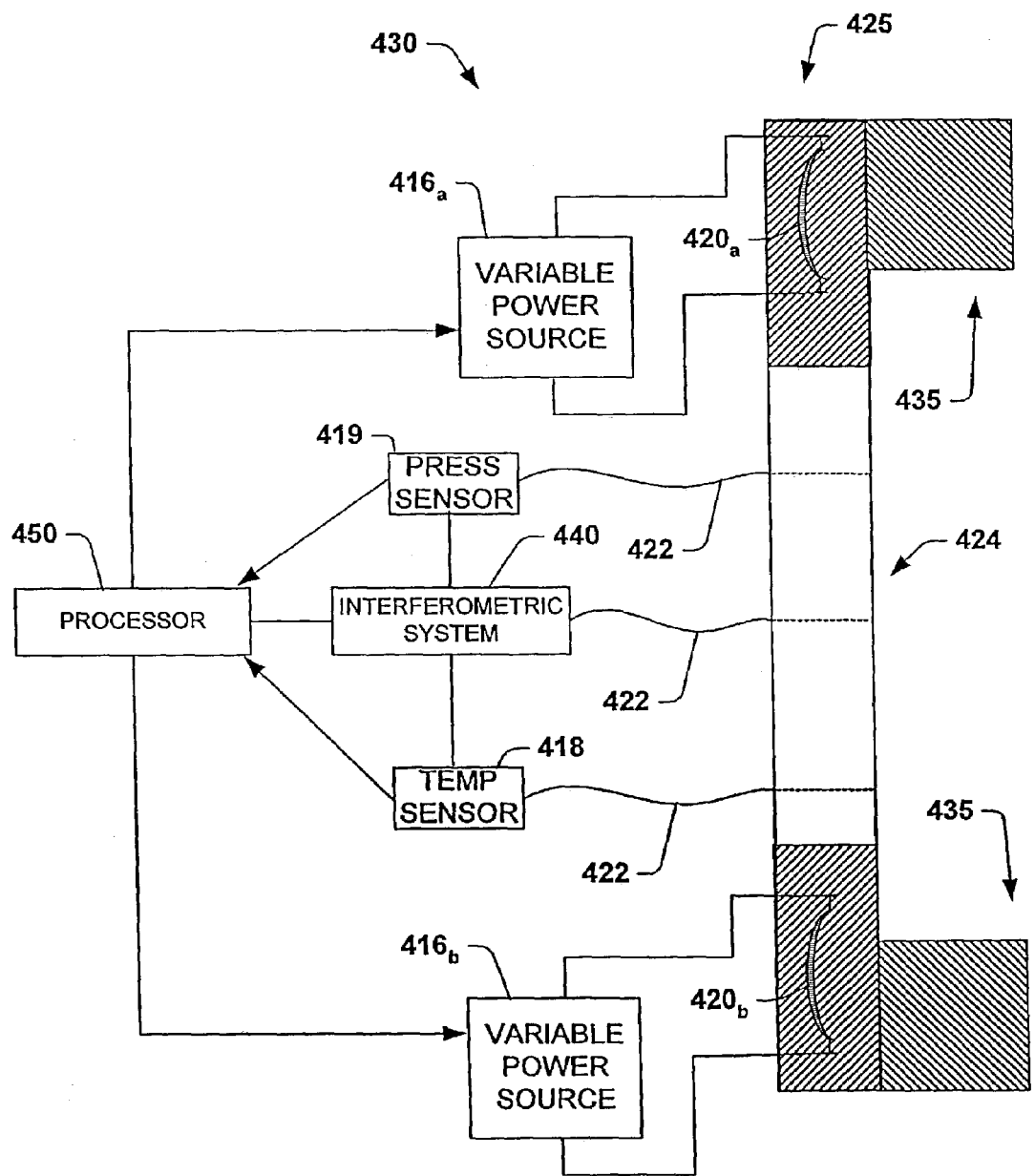
FIG. 18a is a partial schematic diagram illustrating a control system according to the present invention for controlling seal pressure.

Turning now to FIG. 18a, a partial schematic block diagram of a control system 430 is provided. A seal 425 is provided adjacent a contacting surface 435. The seal 425 includes an opening 424 for receiving a shaft of a pump (not shown) or for allowing liquid to flow through the opening 424. A first piezoelectric device $420_a$ is disposed in a first end of the seal 425 contacting a first surface of the contacting surface 435, and a second piezoelectric device $420_b$ is disposed in a second end of the seal 425 contacting a second surface of the contacting surface 435. The first piezoelectric device $420_a$ is coupled to a first variable power source $416_a$ and the second piezoelectric device $420_b$ is coupled to a second variable power source $416_b$. Varying the voltages of the power sources causes flexing of the piezoelectric devices flexing the seal (e.g., expanding or contracting) and thus changing the pressure of the seal ends against the contacting surface 435.

A plurality of optical fibers 422 are embedded within the seal 425 for measuring seal wear, seal environment pressure and temperature environment pressure. An optical fiber 422 is coupled to a pressure sensor 419, which is coupled to an interferometric system 440 and a processor 450 for measuring pressure. An optical fiber 422 is coupled to a temperature sensor 418, which is coupled to the interferometric system 440 and the processor 450 for measuring temperature. An optical fiber 422 is directly coupled to the interferometric system 440 and the processor 450 for measuring seal wear. The processor 450 can utilize any or all of these measurements to adjust the voltage of the variable voltage sources, $416_a$ and $416_b$, and thus the seal pressure based on real time measurements. An opportunity also exists for dynamic real-time control of the seal interface to accommodate circular asymmetry of the shaft and radial shaft misplacement due to for example unbalance and bearing wear.

Figure 18B:
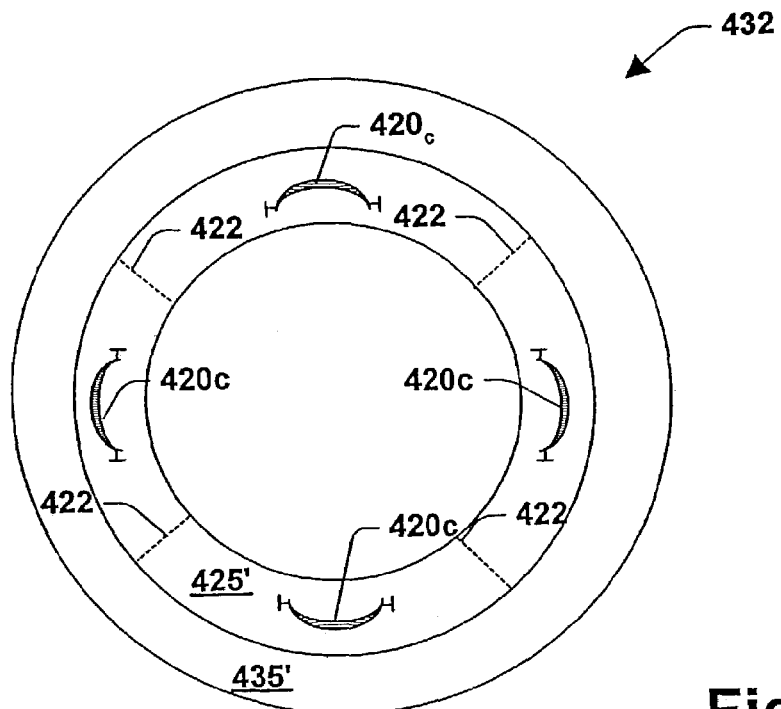
FIG. 18b is a front view of an alternate control system with a seal exposed within a contacting surface according to the present invention.
Figure 18C:
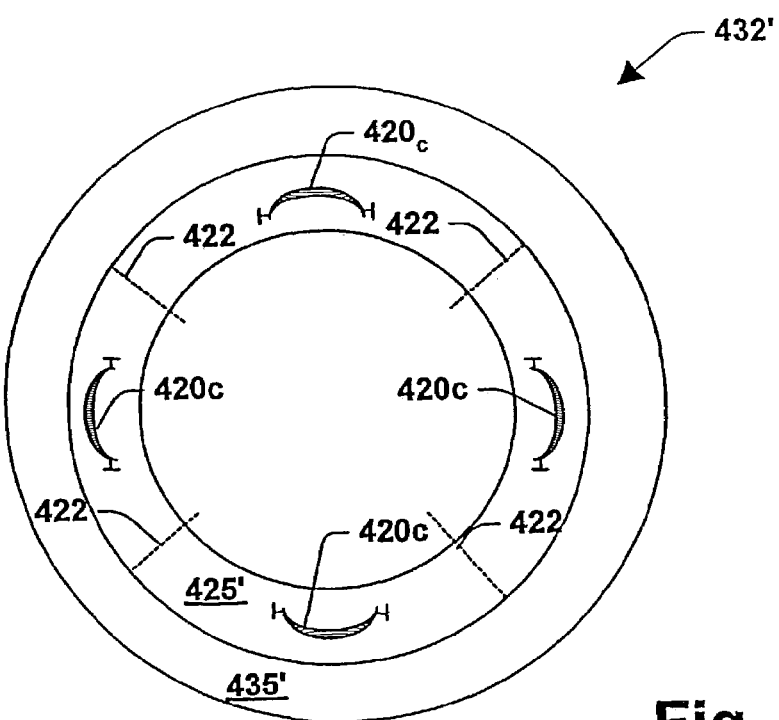
FIG. 18c is a front view of the seal of FIG. 18b with the optical fibers extending outside the seal according to the present invention.

FIG. 18b illustrates a system 432 wherein a seal 425' is disposed radially inboard a contacting surface 435'. A plurality of piezoelectric devices $420_c$ are disposed circumferentially around the seal 425'. A plurality of optical fibers 422 are disposed radially within the seal 425'. The plurality of piezoelectric devices $420_c$ allow for applying axially movable pressure on a shaft (not shown) to increase the contact pressure of the seal on the shaft. Alternatively, the plurality of piezoelectric devices $420_c$ allow for applying pressure on the contacting surface 435'. FIG. 18c illustrates an alternate example of a system 432' having a seal similar to the seal 425', except that the plurality of optical fibers 422 extend outside of the seal 425'.

FIG. 19 illustrates a partial schematic block diagram of an alternate seal control system 500. A seal 510 is provided between a first chamber 520 and a second chamber 530. A piezoelectric device 550 is embedded along a substantial portion of the seal 510. The seal 510 forms a diaphragm between the first chamber 520 and the second chamber 530. An aperture 560 is disposed in the seal 510 for allowing fluid flow between the first chamber 520 and the second chamber 530. The. piezoelectric device 550 is coupled to a power source 516. Varying the voltages of the power source 516 causes flexing of the piezoelectric device and the seal 510 and thus changes the volume of fluid and the fluid pressure within the first chamber 520 and the second chamber 530. An optical fiber 522 is coupled to a pressure sensor 519, which is coupled to an interferometric system 540 and a processor 545 for measuring fluid pressure. The processor 545 can utilize the pressure measurements to adjust the voltage of the variable voltage source 516 and thus flex the piezoelectric device 550 causing the seal 510 to flex which adjusts the fluid pressure in the first chamber 520 and the second chamber 530.

What has been described above are preferred embodiments of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A sensor device comprising:
a seal of a dynamoelectric machine that has at least one optical fiber embedded therein, wherein wear of the optical fiber is representative of continuous wear of the seal.

2. The seal of claim 1, wherein the a length direction of the at least one optical fiber is substantially parallel to a wear direction of the bearing.

3. A method for determining at least one condition of a seal, comprising the steps of:
providing a seal of a dynamoelectric machine having an optical fiber embedded therein; wherein wear of the optical fiber is representative of continuous wear of the seal;
using a measuring system operatively connected to the optical fiber to collect information relating to the seal; and
using a processor operatively coupled to the measuring system to determine the at least one condition of the seal based on the information.

4. The method of claim 3, the at least one condition being seal wear rate.

5. The method of claim 3, the at least one condition being seal temperature environment.

6. The method of claim 3, the at least one condition being seal pressure.

7. The method of claim 3, the at least one condition being seal thickness.

8. The method of claim 3, the at least one condition being seal compression.

9. The method of claim 3, the at least one condition being thermal expansion.

10. The method of claim 3, the at least one condition being deformation.

11. A system that detects a condition relating to a seal, comprising:
one or more optical fibers embedded substantially parallel to a wear direction in a mechanical seal to represent an incessant wear of the seal, wherein the one or more optical fibers contain at least one waveguide employed to measure at least one parameter related to the mechanical seal.

12. The system of claim 11, the one or more optical fibers are doped.

13. The system of claim 11, the parameter is one of: thickness, film variation over time, fluid advancement rate, fluid advancement geometry, contaminants, cavitation, seal advancement rate and shaft wear.

14. The system of claim 11, the one or more optical fiber has a bragg grating employed to measure one of seal compression, thermal expansion and detbrxnation of the seal.

15. The system of claim 11, the seal is an annular seal surrounding a shaft.

16. The system of claim 11, the fiber is oriented with one end that extends through an outer diameter of the seal and the other end extends into the inner diameter of the seal.

17. The system of claim 11, fibers are located at least one of radially, axially, inner circumferentially and outer circumferentially.

18. The system of claim 11, the optical fiber is embedded in one of the lip and undulation portion of the seal.

19. The system of claim 11, a plurality of fibers is utilized to measure characteristics of lubricating film associated with the mechanical seal.

20. The system of claim 15, the one or more optical fibers are employed to measure the radial displacement of the shaft.

21. The system of claim 11, the orientation of the fiber is determinative of the parameter that is measured.

22. The system of claim 11, the one or more optical fiber can vary one of fiber type, fiber orientation, fixturing and doping of the one or more optical fiber.

23. A methodology for measuring wear of a mechanical seal, comprising:
creating a seal of a dynamoelectric machine that has at least one optical fiber embedded therein, wherein wear of the optical fiber is representative of continuous wear of the seal;
measuring one or more parameters relating to the seal utilizing at least one embedded optical fiber;
sending a signal from the at least one embedded optical fiber to a processing component; and
adjusting the seal via the processing component based at least in part upon the signal sent from the at least one embedded optical fiber.

24. The method of claim 23, the signal received by the processing component is one of continuous, periodic and based upon a condition.

25. The method of claim 23, the processing component is an interferometric system.

26. The method of claim 23, the at least one optical fiber employs a grating to measure temperature of the seal.

27. The method of claim 23, the at least one optical fiber contains one or more microbends to measure pressure on the seal.

28. The method of claim 27, further comprising a piezo-based device is employed to provide feedback adjustments to the pressure on the seal.

* * * * *